United States Patent
Lai et al.

(10) Patent No.: US 8,357,701 B2
(45) Date of Patent: Jan. 22, 2013

(54) GALACTOKINASE INHIBITORS

(75) Inventors: Kent Lai, Salt Lake City, UT (US);
Klass Jan Wierenga, Oklahoma City, OK (US); Manshu Tang, Salt Lake City, UT (US)

(73) Assignee: University of Miami, Miami, FL (US)

( * ) Notice: Subject to any disclaimer, the term of this patent is extended or adjusted under 35 U.S.C. 154(b) by 182 days.

(21) Appl. No.: 12/672,347

(22) PCT Filed: Aug. 14, 2008

(86) PCT No.: PCT/US2008/073152
§ 371 (c)(1), (2), (4) Date: Feb. 5, 2010

(87) PCT Pub. No.: WO2009/023773
PCT Pub. Date: Feb. 19, 2009

(65) Prior Publication Data
US 2011/0251236 A1 Oct. 13, 2011

Related U.S. Application Data

(60) Provisional application No. 60/956,012, filed on Aug. 15, 2007, provisional application No. 61/056,545, filed on May 28, 2008.

(51) Int. Cl.
*A61K 31/4709* (2006.01)
*A61K 31/055* (2006.01)
*A61K 31/10* (2006.01)
*A61K 31/343* (2006.01)
*A61P 3/00* (2006.01)
*C40B 30/00* (2006.01)

(52) U.S. Cl. .......... 514/314; 568/726; 568/48; 514/735; 514/454; 514/712; 514/468; 549/223; 549/461

(58) Field of Classification Search .................. 514/314, 514/735, 454, 712, 468; 568/726, 48; 549/223, 549/461
See application file for complete search history.

(56) References Cited

U.S. PATENT DOCUMENTS
2006/0069245 A1 3/2006 Tully et al.
2010/0183583 A1 7/2010 Brace et al.

FOREIGN PATENT DOCUMENTS
WO 2005046610 5/2005
WO 2007002131 1/2007

OTHER PUBLICATIONS

Fridovich-Keil, Journal of Cellular physiology, 209; pp. 701-706, 2006, p. 701.*
Holden et al. (CMLS cell. Mol. Life Sci. vol. 61, 2004, 2471-2484).*
Baselga (Science 26, May 2006, vol. 312. No. 5777, pp. 1175-1178.*
Czarnik, A.W. Encoding methods for combinatorial chemistry; IRORI Quantum Microchemistry; 1:60-66 (1997).
Wu, G. et al. Determining Appropriate Substrate Conversion for Enzymatic Assays in High-Throughput Screening; J Biomol Screen 8: 694-700 (2003).
Wada, T. et al. Crystal Structure of 4-(Cytidine 5'-diphospho)-2-C-methyl-D-erythritol kinase, an Enzyme in the Non-mevalonate Pathway of Isoprenoid Synthesis; The Journal of Biological Chemistry; 278(32), 30022-30027 (2003).

(Continued)

*Primary Examiner* — Savitha Rao
(74) *Attorney, Agent, or Firm* — Novak Druce + Quigg LLP

(57) ABSTRACT

Therapeutic agents for treatment of Galactosemia and disorders thereof, and other enzyme related disorders thereof are identified. The compounds inhibit galactokinase (GALK) and other kinase activity and are identified by a high throughput screening assay.

4 Claims, 14 Drawing Sheets

OTHER PUBLICATIONS

Platt, A. et al. The insertion of two amino acids into a transcriptional inducer converts it into a galactokinase; PNAS; 97(7) (2000).

Thoden, J. B. et al. Molecular Structure of Human Galactokinase; The Journal of Biological Chemistry; 280(10); 9662-967 (2005).

Timson, D.J. et al. Functional analysis of disease-causing mutations in human galactokinase; Eur. J. Biochem. 270, 1767-1774 (2003).

DeWitt, S.H. et al. Diversomers: An approach to nonpeptide, nonoligomeric chemical diversity; Proc. Natl. Acad. Sci. USA; vol. 90, 6909-6913 (1993).

Abstract—Discovery of enzyme inhibitors through combinatorial chemistry; Mol Divers 2(4) 223-236 (1997).

Seiler, K.P. et al. ChemBank: a small-molecule screening and cheminformatics resource database; Nucleic Acids Research, vol. 36, 351-D359 (2008).

Liang, R. et al. Parallel Synthesis and Screening of a Solid Phase Carbohydrate Library; Science, vol. 274, 1520-1522 (1996).

Heinrich et al., Galactokinase, Methods Enzymol. 407-412, 1991, Wiley-Lissm Inc.

Tang, M., et al., Molecular and Biochemical Characterization of Human Galactokinase and its small molecule inhibitors, Chem Biol Interact. Dec. 5, 2010; 1883(3): 376-385.

\* cited by examiner

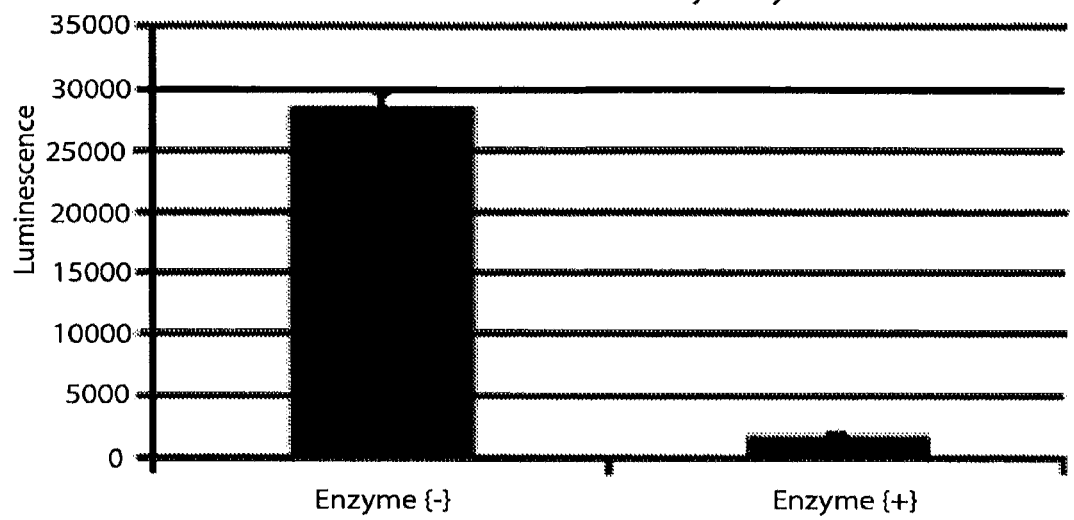

GALACTOKINASE INHIBITORS

CROSS-REFERENCE TO PRIOR APPLICATION

This is the U.S. National Phase Application under 35 U.S.C. §371 of International Application no. PCT/US08/73152, filed Aug. 14, 2008, which claims the benefit of U.S. Provisional Patent Application Nos. 60/956,012, filed Aug. 15, 2007 and 61/056,545, filed May 28, 2008, all of which are incorporated by reference in their entireties. The International Application was published in English on Feb. 19, 2009 as WO/2009/023773 under PCT Article 21 (2).

CLAIM FOR PRIORITY

This application claims priority to U.S. Provisional Application Nos. 60/956,012, filed Aug. 15, 2007, and 61/056,545, filed May 28, 2008, both of which are incorporated by reference herein in their entireties.

STATEMENT REGARDING FEDERALLY SPONSORED RESEARCH

This invention was made with U.S. government support under grant number R01 HD054744-01 awarded by the National Institutes of Health. The U.S. government has certain rights in the invention.

FIELD OF THE INVENTION

This invention relates to compounds that inhibit galactokinase (GALK) and other kinases and the development of a high-throughput screening assays to identify galactokinase and other kinase inhibitors.

BACKGROUND

Classic Galactosemia is an inherited metabolic condition caused by deficiency of galactose-1-phosphate uridylyltransferase (GALT, EC 2.7.7.12) activity. GALT is the second enzyme in the evolutionarily conserved galactose (Leloir) metabolic pathway, and facilitates the simultaneous conversion of uridine diphosphoglucose (UDP-glucose) and galactose-1-phosphate (gal-1-p) to uridine diphosphogalactose (UDP-galactose) and glucose-1-phosphate. Consequently, GALT deficiency leads to the unique accumulation of gal-1-p and deficiency of UDP-galactose in patient cells. If untreated, Classic Galactosemia can result in severe disease in the newborn period, including direct hyperbilirubinemia, quickly progressing to acute liver failure, coagulopathy, coma and death. Ever since most states in the USA included Classic Galactosemia in the newborn screening panel, neonatal morbidity and mortality have decreased considerably. The current mainstay of treatment is the withdrawal of (ga-)lactose from the diet.

However, it has become clear that despite optimal dietary management, chronic complications such as IQ deficits, ataxia, speech dyspraxia, and premature ovarian failure persist, and that gal-1-p remains elevated in patients with Classic Galactosemia. The pathogenic mechanisms for the chronic complications remain uncertain, but several lines of evidence strongly suggested that the chronically elevated gal-1-p is the major contributor to the long-term sequelae of Classic Galactosemia. Firstly, except for cataracts, patients with inherited deficiency of galactokinase (GALK, E.C. 2.7.1.6) (OMIM 230200) do not accumulate gal-1-p, and do not experience the range of complications seen in GALT-deficient patients. Secondly, while a gal1-deleted (i.e., GALT-deficient) yeast stops growing upon addition of galactose to the growth medium, a gal7 gal1 double knock-out strain deficient in both GALT and GALK enzyme activities is no longer sensitive to galactose. Thirdly, our laboratory recently demonstrated that galactose challenge to isogenic GALT-deficient (but not GALK-deficient) yeast led to overt manifestation of environmental stress response (ESR). All these studies strongly indicate that gal-1-p is the major, if not sole, culprit for the galactose toxicity observed in GALT-deficient cells.

This raises the question about the origin of gal-1-p, the enzymatic product of galactokinase (GALK) on galactose, in a galactosemic patient who refrains from dairy products. It has been found that galactose moieties converted to gal-1-p can also come from non-dairy sources, e.g. galactose-containing fruits and vegetables amounting to as much as 30 mg/day. However, galactose moieties can also be produced endogenously from UDP-glucose via the UDP-4-galactose epimerase (GALE) reaction, as well as from the natural turnover of glycolipids and glycoproteins. In fact, using isotopic labeling, it was shown that a 50 kg adult male could produce up to 1.2 grams of galactose per day, which is many times of the amount of exogenous galactose potentially present in galactose-restricted diets. Therefore, endogenous synthesis of galactose is likely to undermine the efficacy of dietary management as standard therapy. Since endogenous galactose production is not amenable to dietary manipulation, there is a need for innovative, non-dietary therapy.

SUMMARY

Compositions for inhibiting or modulating kinases are provided. A method of identifying and screening newly identified compositions is described. High-throughput screening assays described herein provide an accurate, fast and efficient way in which to identify and screen compounds with diverse structures.

In a preferred embodiment, a compound comprises at least one of: HSCI1__000333 Calbiochem 540215 (Tyrosine Phosphatase CD45 inhibitor); K04__097174 582836 Neumann; TimTec1__006661TimTec ST4094742; HSCI1__000182 Calbiochem 428022 (β-Lapachone); ChemDiv3__007091 ChemDiv 7218-1573; ChemDiv3__000368 ChemDiv 1184-1682; TimTec1__001881 TimTec ST026634; ChemDiv3__002016 ChemDiv 3553-1484; SPBio__001210 (Hexachlorophene); SMP2__000049 Sigma E9259 (Erythrosin B); ChemDiv3__007133 ChemDiv 7218-1483; TimTec1__001324 TimTec ST014236; ChemDiv3__007089 ChemDiv 7218-1459; Maybridge4__001932 JFD03061; TimTec1__000233 TimTec ST000572; ChemDiv3__014119 ChemDiv 7218-1576; ChemDiv3__001694 ChemDiv 3241-0272; SPBio__000126 Spectrum2__000113 (Bithionol); SPBio__001697 Spectrum2__001629 (Rhodomyrtoxin); ChemDiv3__002334 ChemDiv 3696-0201; ChemDiv3__000903 ChemDiv 1887-0088; TimTec1__001108 TimTec ST014268; Maybridge4__001288 HTS01859; SMP2__000320 Sigma S1014 (Streptonigrin); TimTec1__001055 TimTec ST012305; ChemDiv3__001508 ChemDiv 3229-1543; ChemDiv3__007160 ChemDiv 8012-2663; ChemDiv3__001677 ChemDiv 3062-0036; TimTec1__003525 TimTec ST048025; BiomolKI2__000062 BiomolEI-307; ChemDiv3__001693 ChemDiv 3175-0337; TimTec1__002320 TimTec ST032682; ChemDiv3__003365 ChemDiv 4456-1104; TimTec1__005567 TimTec ST4029573, HSCI1__000305 (NF279), ChemDiv3__002459, HSCI1__000035, PK04__097255, PK04__098179, SCI1__000331, HSCI1__000187, Maybridge4__003162, ACon1__002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175, substitutes, variants, isomers, salts and analogs thereof.

In another preferred embodiment, the one or compounds are present in therapeutically effective amounts. In one aspect the ratio of the compounds in the composition are adjusted to a specific patient's needs. Thus the compounds can be in a 1:1:1 etc ratio or 1:2:4:5:1 etc ratio.

In another preferred embodiment a high throughput screening assay comprises measuring GALK activity by determining the amount of ATP remaining after completion of the GALK-mediated reaction (step 1): Galactose+ATP→gal-1-p+ADP; and measuring luminescence in a luciferase reaction (step 2): ATP+Luciferin & Luciferase→oxyluciferin+light.

In another preferred embodiment, the kinase inhibitors comprise inhibitors of individual kinases, groups of kinases and superfamilies of kinases. Examples include but not limited to Galactose Homoserine Mevalonic acid Phosphomevalonic acid (GHMP) kinases, nucleoside monophosphate (NMP) kinase; WNK kinases; and MAPK (mitogen-activated protein kinase) super-families; individual kinases comprise galactokinase, homoserine kinase, mevalonate kinase, phosphomevalonate kinase, CDP-ME kinase, N-acetylgalactosamine kinase, mevalonate 5-diphosphate decarboxylase, and arabinose kinase.

In another preferred embodiment, a method of treating Classic Galactosemic patients comprises administering to a patient in thereof, a composition comprising one or more agents in a therapeutically effective amount, comprising: HSCI1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin); ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 Chembiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573, HSCI1_000305, ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, PK04_097175, variants, analogs, isomaers, salts and substituents thereof. Administration of one or more agents modulate or inhibit galactokinase (GALK) production and/or activity.

In another preferred embodiment, the compounds of the invention are isomers, tautomers and combinations thereof.

In another preferred embodiment, a method of monitoring GALK activity in a patient comprises obtaining a biological sample from a patient; subjecting the sample to a high throughput screening assay wherein said assay comprising determining amount of ATP remaining after completion of the GALK-mediated reaction (step 1): Galactose+ATP→gal-1-p+ADP; and measuring luminescence in a luciferase reaction (step 2): ATP+Luciferin & Luciferase→oxyluciferin+light.

In another preferred embodiment, a method of determining drug efficacy in treating patients suffering from galactosemia comprises obtaining a biological sample from a patient; subjecting the sample to a high throughput screening assay comprising determining amount of ATP remaining after completion of the GALK-mediated reaction (step 1): Galactose+ATP→gal-1-p+ADP; and measuring luminescence in a luciferase reaction (step 2): ATP+Luciferin & Luciferase→oxyluciferin+light.

In another preferred embodiment, a method of modulating or inhibiting one or more kinases in a patient or cell, comprises administering to a patient in thereof, a composition one or more agents in a therapeutically effective amount, comprising: HSCI1_000305, ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, PK04_097175, variants, analogs, isomers, salts and substituents thereof.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 3A shows the effect of varying amounts of adenosine triphosphate (ATP) and enzyme on GALK activity. GALK reaction was carried out at different ATP concentrations (5, 10, 20 μM) and different GALK amount (0, 0.05, 0.1, 0.15, 0.3 μg) in a final volume of 30 μL. Each condition was carried out in 48 replicates (n=48). At the end of the reaction time (60 min), 30 μL of Kinase-Glo™ reagent was added. Luminescence was recorded as relative luminescence units (RLU) 10 min thereafter. Absolute luminescence values for different amounts of ATP standards (without GALK and galactose) were also determined using the Kinase-Glo™ reagent, and this information was used to convert the raw RLU to the amount of ATP remaining at the end of the reaction. Each data point represents the mean of 48 replicates. Error bars represent ±1 SD. The experiment was repeated twice to confirm reproducibility. FIG. 3B is a graph showing Z' factor determination. A 384-well plate was divided into 176 wells each for samples and controls, leaving the 2 center columns (32 wells) empty to prevent crossover of luminescence signals. To the sample wells, 0.15 μg GALK was added in the presence of 5 μM ATP and 3 mM galactose in a final volume of 30 μL. In the control wells, GALK was omitted, but other reaction conditions remained identical. Reaction was carried out at room temperature for 60 min. At the end of the reaction, 30 μL of Kinase-Glo™ reagent was added. Luminescence was recorded as RLU after 10 min. Each data point on the graph represents the luminescence recorded for each well. The mean and the standard deviation were calculated for the samples and controls. Sample/control ±3 SD were plotted around each data point. The experiment was repeated 3 times to confirm reproducibility. FIG. 3C is a graph showing inhibition of GALK activity by ATP-γ-S. GALK activity was assayed in HTS format in the presence of varying amount of ATP-γ-S (squares). To control for potential inhibition of luciferase reaction by ATP-γ-S, a separate GALK assay with GALK omitted was performed (diamonds). Error bars represent ±1 SD (n=32).

FIG. 9 is a photograph of a gel showing the purification of recombinant E. coli CDP-ME kinase. Over-expression of the bacterial CDP-ME kinase was induced in E. coli HMS174 cells harboring the plasmid expressing the E. coli IspE gene (lanes 2 to 5). The over-produced CDP-ME kinase witnessed in the lysate of the bacteria (marked by ⊕ in lane 2) was purified by Nickel affinity chromatography and collected in the eluate lane 5 (also marked by ⊕). FT: Flow-through.

FIG. 10A is a graph showing the validation of CDP-ME kinase assay. A two-step luminescence-based assay was used to test the activity of purified CDP-ME kinase by measuring the amount of ATP left in the reaction. Panel (a) showed that in the presence of active CDP-ME kinase, ATP was used up in the CDP-ME kinase reaction (first step), leaving little for the luciferase-luciferin reaction in step 2.

DETAILED DESCRIPTION

Figure 1:
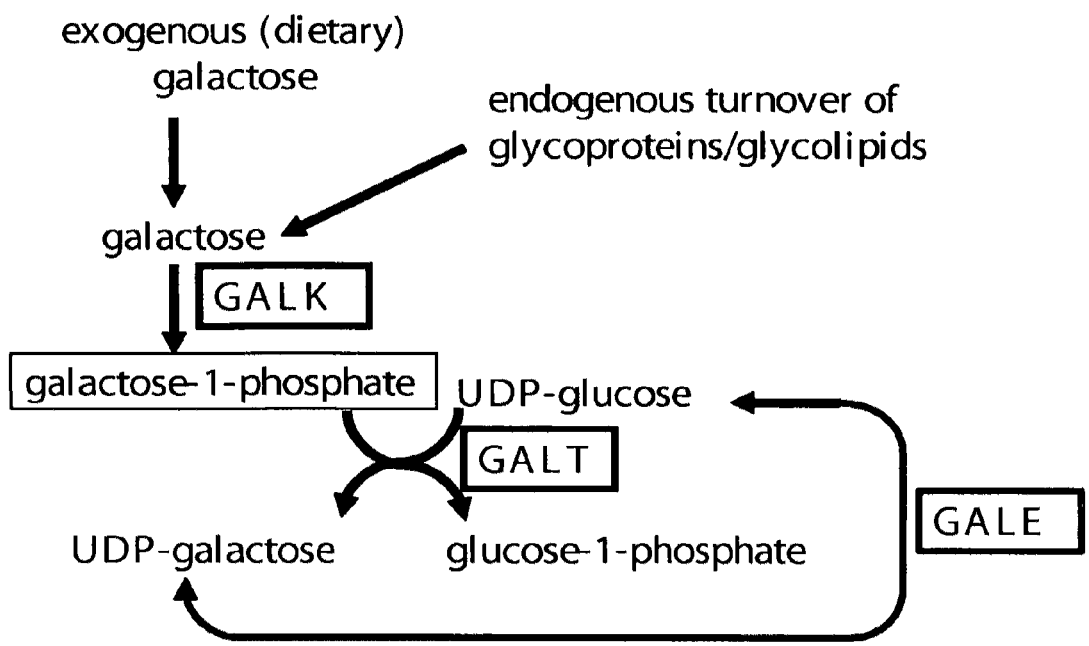
FIG. 1 is a schematic illustration showing the human galactose metabolic pathway. Exogenous and endogenously produced α-D-galactose is phosphorylated by galactokinase (GALK) to form galactose-1-phosphate (gal-1-p) (highlighted). In the presence of galactose-1-phosphate uridyl-transferase (GALT), galactose-1-phosphate will react with uridine diphosphoglucose (UDP-glucose) to form glucose-1-phosphate and uridine diphosphogalactose (UDP-galactose). UDP-galactose can also be formed from UDP-glucose via the UDP galactose-4'-epimerase (GALE) reaction. ATP, adenosine triphosphate; ADP, adenosine diphosphate.

The invention comprises novel therapeutic small molecule inhibitors of the human enzyme galactokinase (GALK) and other kinases. A high-throughput in vitro assay that was developed and used to screen against libraries that contain nearly 50,000 small molecule compounds. The assay is a robust, miniaturized high-throughput screening assay that is able to identify compounds with highly diverse structural compositions.

DEFINITIONS

As used herein, "a", "an," and "the" include plural references unless the context clearly dictates otherwise.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cyclic amine" is a hydrocarbon ring wherein one carbon atom of the ring has been replaced by a nitrogen atom. The cyclic amine can be unsaturated, partially saturated, or fully saturated. The cyclic amine can also be bicyclic, tricyclic, and polycyclic. Examples of cyclic amine include pyrrolidine and piperidine.

Halo" or "halogen" refers to fluoro, chloro, bromo, and iodo.

"Counterion" is used to represent a small, negatively charged species, such as chloride, bromide, hydroxide, acetate, and sulfate.

"Carbocycle" is any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms (e.g., one or two carbon atom bridges). A bridge always converts a monocyclic ring into a tricyclic ring. When a ring is bridged, the substituents recited for the ring may also be present on the bridge.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heterocycle" refers to any stable 5, 6, or 7-membered monocyclic or bicyclic or 7, 8, 9, or 10-membered bicyclic heterocyclic ring that is saturated, partially unsaturated, or unsaturated (aromatic), and consisting of: carbon atoms and 1, 2, 3, or 4 ring heteroatoms independently selected from the group consisting of N, O and S and including any bicyclic group in which any of the above-defined heterocyclic rings is fused to a benzene ring. The N group may be N, NH, or N-substituent, depending on the chosen ring and if substituents are recited. The nitrogen and sulfur heteroatoms may optionally be oxidized (e.g., S, S(O), S(O)$_2$, and N—O). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Typically, the total number of S and O atoms in the heterocycle is not more than 1. Bridged rings are also included in the definition of heterocycle. A bridged ring occurs when one or more atoms (i.e., C, O, N, or S) link two non-adjacent carbon or nitrogen atoms. Examples of bridges include one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heterocycles include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

"Mammal" and "patient" cover warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat an indication listed herein. "Therapeutically effective amount" also includes an amount of the combination of compounds claimed that is effective to treat the desired indication. The combination of compounds can be a synergistic combination. Synergy, as described, for example, by Chou and Talalay; *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

The compounds of the invention encompass various isomeric forms. Such isomers include, e.g., stereoisomers, e.g., chiral compounds, e.g., diastereomers and enantiomers, e.g. racemates. "Racemate" is an equimolar mixture of a pair of enantiomers. A racemate does not exhibit optical activity. The chemical name or formula of a racemate is distinguished from those of the enantiomers by the prefix (±)- or rac- (or racem-) or by the symbols RS and SR.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

Furthermore the indication of configuration across a carbon-carbon double bond can be "Z" referring to what is often referred to as a "cis" (same side) conformation whereas "E" refers to what is often referred to as a "trans" (opposite side) conformation. Regardless, both configurations, cis/trans and/or Z/E are contemplated for the compounds for use in the present invention.

With respect to the nomenclature of a chiral center, the terms "d" and "l", "R" and "S", configuration are as defined by the IUPAC Recommendations. As to the use of the terms, diastereomer, racemate, epimer and enantiomer, these will be used in their normal context to describe the stereochemistry of preparations.

Development of High-Throughput Assay

Traditionally, the measurement of GALK employs the three-step enzyme-linked assay that involves pyruvate kinase and lactic dehydrogenase in a final volume greater than 500 µl. A two-step luciferase-based assay was developed as a high-throughput (384 well plate) format. The principle behind this assay is as follows:

Step 1:

Galactose + ATP $\xrightarrow{\text{GALK}}$ Galactose-1-phosphate

Step 2:

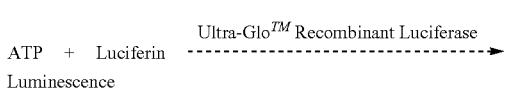
ATP + Luciferin $\xrightarrow{\text{Ultra-Glo}^{TM}\text{ Recombinant Luciferase}}$ Luminescence If there is ample GALK activity, ATP is used up in step 1 and little is left for the luciferase reaction in step 2. Consequently, the more active GALK reaction, the less luminescence is recorded.

Screening for small molecule inhibitors of human galactokinase (GALK) and other kinase inhibitors: This high throughput assay was then used to screen against various compound libraries in order to identify compounds that inhibit GALK activity. From a total of about 50,000 compounds, the top 150 compounds were selected and ranked based on their abilities to inhibit the GALK reaction in vitro, for secondary screening (re-test).

The assay was used to screen for other kinase inhibitors, initially from the superfamily of small molecule kinases, also known as the GHMP (Galactose, Homoserine, Mevalonic acid, Phosphomevalonic acid) kinases. Examples within this superfamily include, but not limited to: galactokinase, homoserine kinase, mevalonate kinase, phosphomevalonate kinase, CDP-ME kinase, N-acetylgalactosamine kinase, mevalonate 5-diphosphate decarboxylase, and arabinose kinase.

Other superfamilies and kinases that are comprised within these superfamilies are within the scope of the invention. Examples of superfamilies and other kinases include, but not limited to: nucleoside monophosphate (NMP) kinase; WNK kinases; MAPK (mitogen-activated protein kinase) superfamily which is composed of three major sets of kinases: the extracellular-receptor kinases (ERK) include ERK1; ERK2; ERK3/ERK4, ERK5, and two types of MAPK-related kinases that respond to cellular stress and inflammatory signal: the c-Jun N-terminal kinases/stress-activated protein kinases (JNK/SAPK) which include JNK1, JNK2 and JNK3 and the p38 MAPKinases: p38alpha, p38beta2, p38gamma and p38delta.

Other kinases and families thereof can be screened for candidate kinase inhibitors using the methods described herein.

In another preferred embodiment, the kinases and inhibitors thereof, can be from any source including any living species. Further, the kinase inhibitors can be synthetic, which would include any newly discovered compounds.

Compositions

The compounds may be identified either by their chemical structure and/or chemical name. When the chemical structure and chemical name conflict, the chemical structure is determinative of the identity of the compound. The compounds are intended to include all salts, hydrates, solvates, complexes, derivatives, metabolites and prodrugs, unless the context requires otherwise. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure), enantiomeric and stereoisomeric mixtures, including racemic mixtures. Enantiomeric and stereoisomeric mixtures can be resolved into their component enantiomers or stereoisomers using separation techniques or chiral synthesis techniques well known to the skilled artisan. The chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^{2}H$, $^{3}H$, $^{13}C$, $^{14}C$, $^{15}N$, $^{17}O$ and $^{18}O$. Compounds may exist in unsolvated forms as well as solvated forms, including hydrated forms and as N-oxides. In general, the hydrated, solvated and N-oxide forms are within the scope of the present disclosure. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

Another aspect is a radiolabeled compound of any of the formulae delineated herein. Such compounds have one or more radioactive atoms (e.g., $^{3}H$, $^{2}H$, $^{14}C$, $^{13}C$, $^{35}S$, $^{32}P$, $^{125}I$, $^{131}I$) introduced into the compound. Such compounds are useful for drug metabolism studies and diagnostics, as well as therapeutic applications.

In another preferred embodiment, the compounds identified include prodrugs. The term "prodrug" includes compounds with moieties, which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19; Silverman (2004) The Organic Chemistry of Drug Design and Drug Action, Second Ed., Elsevier Press, Chapter 8, pp. 497-549). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halogen, or methoxy substituents) aryl and aryl-lower alkyl esters, amides, lower-alkyl amides, di-lower alkyl amides, and hydroxy amides. Other prodrug moieties include propionoic and succinic acid esters, acyl esters and substituted carbamates. Prodrugs which are converted to active forms through other mechanisms in vivo are also included.

In a preferred embodiment, a composition comprises one or more of HSCI1__000333 Calbiochem 540215 (Tyrosine Phosphatase CD45 inhibitor); K04__097174 582836 Neumann; TimTec1__006661TimTec ST4094742; HSCI1__000182 Calbiochem 428022 (β-Lapachone); ChemDiv3__007091 ChemDiv 7218-1573; ChemDiv3__000368 ChemDiv 1184-1682; TimTec1__001881 TimTec ST026634; ChemDiv3__002016 ChemDiv 3553-1484; SPBio__001210 (Hexachlorophene); SMP2__000049 Sigma E9259 (Erythrosin B); ChemDiv3__007133 ChemDiv 7218-1483; TimTec1__001324 TimTec ST014236; ChemDiv3__007089 ChemDiv 7218-1459; Maybridge4__001932 JFD03061; TimTec1__000233 TimTec ST000572; ChemDiv3__014119 ChemDiv 7218-1576; ChemDiv3__001694 ChemDiv 3241-0272; SPBio__000126 Spectrum2__000113 (Bithionol); SPBio__001697 Spectrum2__001629 (Rhodomyrtoxin); ChemDiv3__002334 ChemDiv 3696-0201; ChemDiv3__000903 ChemDiv 1887-0088; TimTec1__001108 TimTec ST014268; Maybridge4__001288 HTS01859; SMP2__000320 Sigma S1014 (Streptonigrin); TimTec1__001055 TimTec ST012305; ChemDiv3__001508 ChemDiv 3229-1543; ChemDiv3__007160 ChemDiv 8012-2663; ChemDiv3__001677 ChemDiv 3062-0036; TimTec1__003525 TimTec ST048025; BiomolKI2__000062 BiomolEI-307; ChemDiv3__001693 ChemDiv 3175-0337; TimTec1__002320 TimTec ST032682; ChemDiv3__003365 ChemDiv 4456-1104; TimTec1__005567 TimTec ST4029573, HSCI1__000305 (NF279), ChemDiv3__002459, HSCI1__000035, PK04__097255, PK04__098179, SCI1__000331: HSCI1__000187, Maybridge4__003162, ACon1__002474, Maybridge4__002460, HSCI1__000002, ACon1__001911, SMP2__000091, ChemDiv3__006723, ChemDiv3__000237, PK04__097046, PK04__097081, HSCI1__000004, ChemDiv3__015769, PK04__097057, TimTec1__000037, SPBio__000035, PK04__098125, SPBio__000341, PK04__097018, HSCI1__000315, PK04__097253, ChemDiv3__014394, SPBio__000394, SPBio__000649, ChemDiv3__001455, ChemDiv3__003258, ChemDiv3__002419, PK04__097003, ChemDiv3__000127, ACon1__001054, ChemDiv3__000428, Maybridge4__000719, PK04__097149, PK04__097012, PK04__097295, Maybridge4__000547, Maybridge4__000383, HSCI1__000319, ChemDiv3__012072, SPBio__000927, SPBio__000031, HSCI1__000222, PK04__098045, ChemDiv3__011472, Maybridge4__000280, HSCI1__000113, TimTec1__002292, SPBio__000029, Maybridge4__000025, SPBio__000260, TimTec1__006170, HSCI1__000274, PK04__098207, SPBio__001687, ChemDiv3__000631, SPBio__000023, PK04__097102, Maybridge4__001879, SPBio__002863, ChemDiv3__012460, ChemDiv3__014894, Maybridge4__002594, HSCI1__000296, PK04__

098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175.

The compounds can be administered in combination with other treatments, including and without limitation ratios of the compounds in a therapeutic formulation. For example, at least two compounds can be formulated in a 1:1 ratio v/v or w/w. In another preferred embodiment, the compounds can be in a 1:2 ratio, a 1:3 ratio and the like. In other embodiments, more than two or three or four etc compounds can be formulated in varying ratios to each other. A skilled practitioner would be able to identify the disease and appropriate combination and ratios of compounds to administer a patient.

In another embodiment, the present invention provides novel pharmaceutical compositions, comprising: a pharmaceutically acceptable carrier and a therapeutically effective amount of a compound of the present invention or a pharmaceutically acceptable salt form thereof.

Non-limiting examples of the structures of some compounds include:

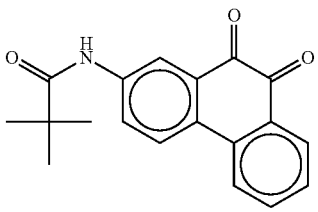

1

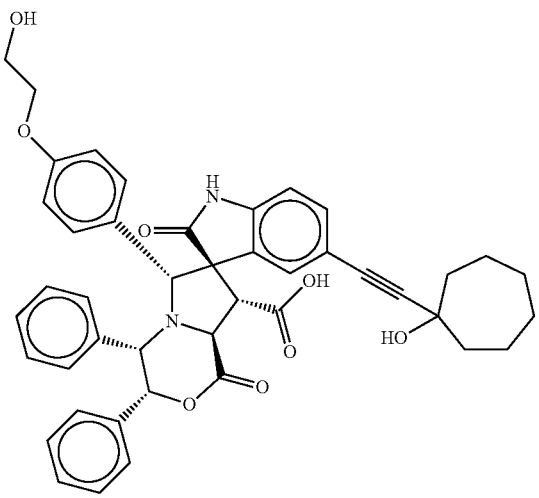

2

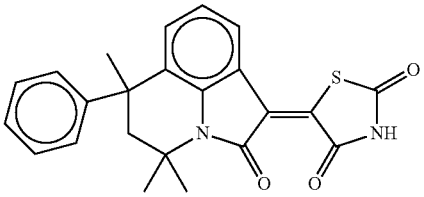

3

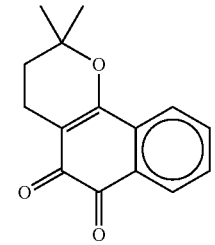

4

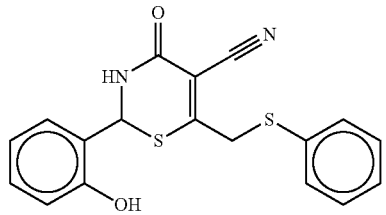

5

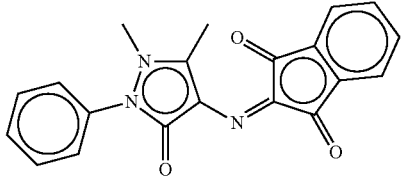

6

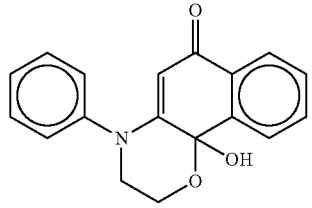

7

17
-continued
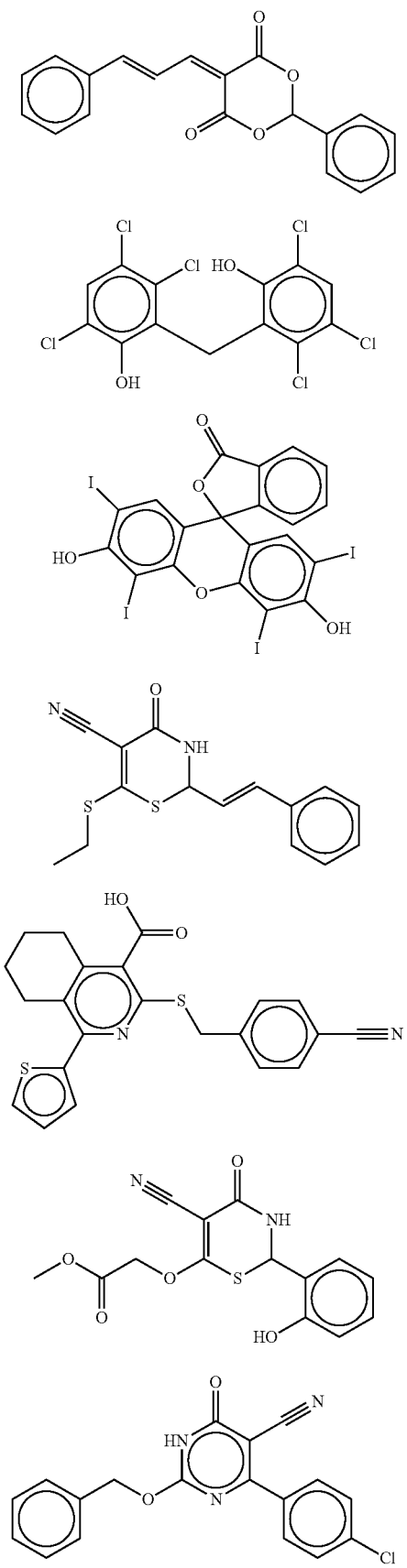
18
-continued
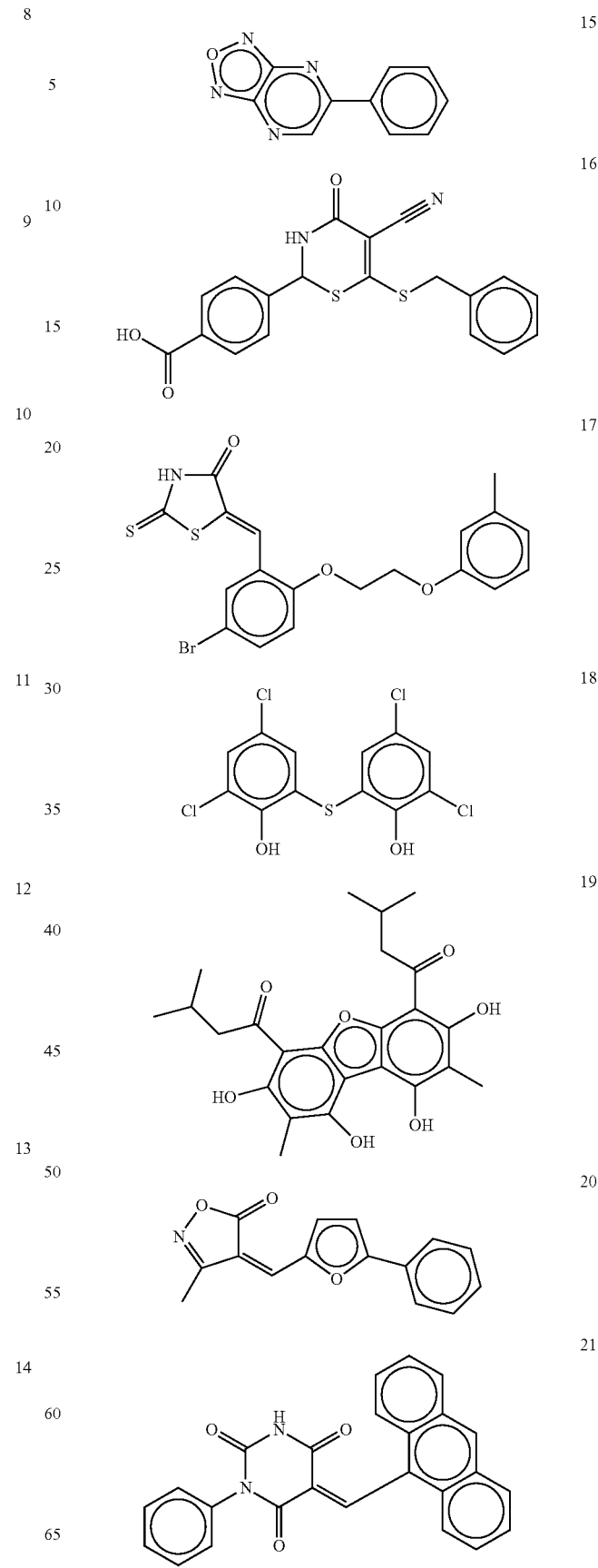

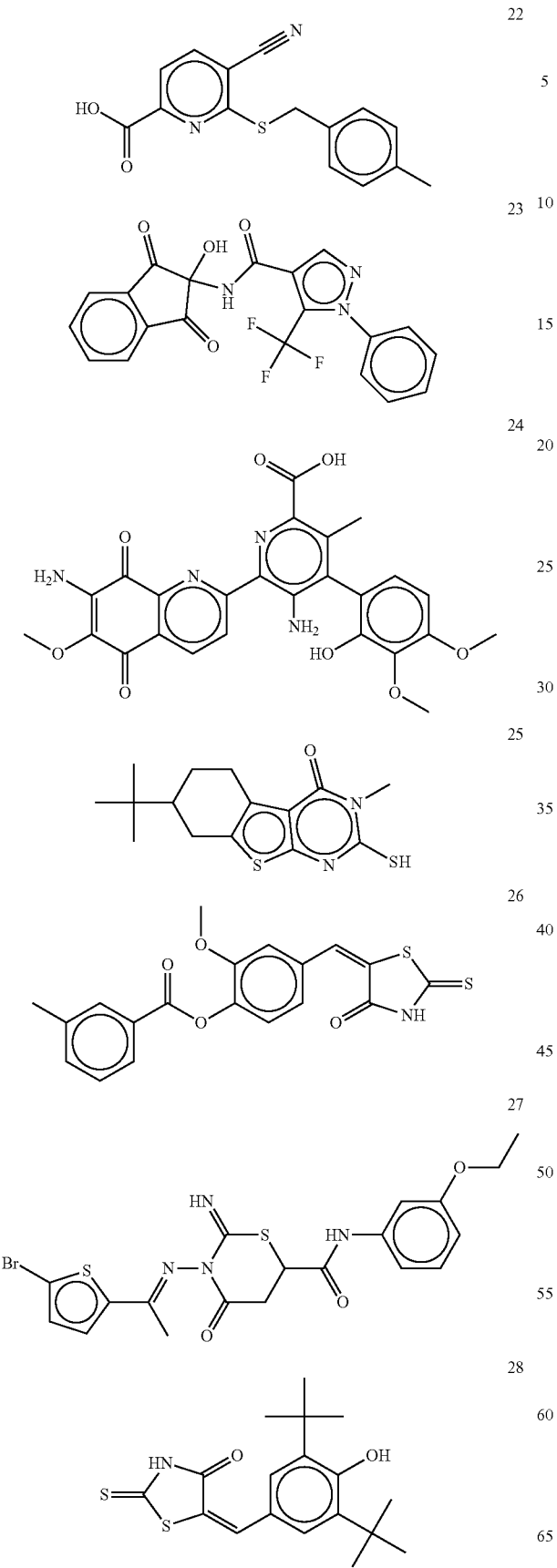
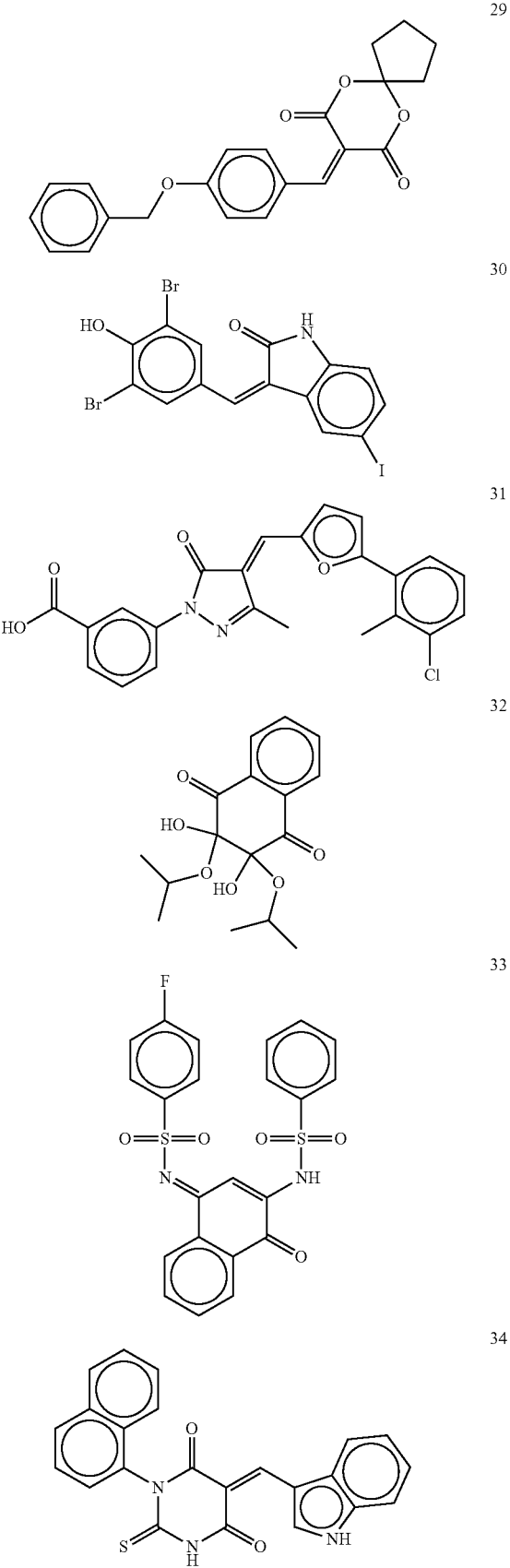

In preferred embodiments, the compounds comprise analogs.

In another preferred embodiment, the compounds comprise one or more substitutions or modifications. The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. Isotopes of hydrogen include tritium and deuterium. Isotopes of carbon include C-13 and C-14.

When any variable occurs more than one time in any constituent or formula for a compound, its definition at each occurrence is independent of its definition at every other occurrence. Thus, for example, if a group is shown to be substituted with 0-2 of a certain group, say, for example the group is designated as "X", then said group may optionally be substituted with up to two X groups and X at each occurrence is selected independently from the definition of X. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

Examples of groups which can be used to substitute any one or more positions of any of the compounds include, but not limited to: H, Cl, F, Br, I, $CF_3$, $OCF_3$, $C_{1-6}$ alkyl substituted with 0, 1 or more of X, $C_{2-6}$ alkenyl substituted with 0, 1 or more of X, $C_{2-6}$ alkynyl substituted with 0, 1 or more of X, $(CH_2)_pNO_2$, $(CH_2)_pCN$, $(CH_2)_pOR$, $(CH_2)_pNR_2$, $(CH_2)_pCOR$, $(CH_2)_pOCOR$, $(CH_2)_pCO_2R$, $(CH_2)_pCONR_2$, $(CH_2)_pOCONR_2$, $(CH_2)_pNRCOR$, $(CH_2)_pNRCO_2R$, $(CH_2)_pNRCONR_2$, $(CH_2)_pC(=NH)NH_2$, $(CH_2)_pSO_2R$, $(CH_2)_pSO_2NR_2$, $(CH_2)_pNRSO_2R$, $(CH_2)_pNRSO_2NR_2$, $(CH_2)_p$-3-10 membered carbocycle substituted with 0, 1 or more of X, and a $(CH_2)_p$-4-10 membered heterocycle substituted with 0, 1 or more of X and consisting of: carbon atoms and 1-4 heteroatoms selected from O, $S(O)_q$, and N; $C_{1-4}$ alkyl, $C_{2-4}$ alkenyl, $C_{2-4}$ alkynyl, $NO_2$, —CN, $OR^a$, $NR^a_2$, $COR^a$, $CO_2R^a$, and $CONR^a_2$; H, $CH_3$, $CH_2CH_3$; a 3-10 membered carbocycle substituted with 0, 1 or more of X and a 5-10 membered heterocycle substituted with 0, 1 or more of X and consisting of: carbon atoms and 1-4 heteroatoms selected from O, $S(O)_q$, and N.

X is selected from O, Cl, F, Br, I, $CF_3$, $OCF_3$, $C_{1-4}$ alkyl, $C_{2-4}$ alkenyl, $C_{2-4}$ alkynyl, $NO_2$, —CN, $OR^a$, $NR^a_2$, $COR^a$, $CO_2R^a$, $CONR^a_2$, $NR^aCOR^a$, $NR^aCO_2R^a$, $NR^aCONR^a_2$, $C(=NH)NH_2$, $SO_2R^a$, $SO_2NR^a_2$, $NR^aSO_2R^a$, $NR^aSO_2NR^a_2$, $(CH_2)_p$-3-10 membered carbocycle substituted with 0-2 $R^b$, and a $(CH_2)_p$-5-10 membered heterocycle substituted with 0-2 $R^b$ and consisting of: carbon atoms and 1-4 heteroatoms selected from O, $S(O)_q$, and N.

$R^a$ is independently selected from H, $C_{1-4}$ alkyl, $C_{3-6}$ cycloalkyl, $CH_2$—$C_{3-6}$ cycloalkyl, phenyl, and benzyl; optionally, $NR^a_2$ forms a 5-6 membered cyclic amine;

$R^b$ is independently selected from H, Cl, F, Br, I, $CF_3$, $OCF_3$, $C_{1-4}$ alkyl, $C_{2-4}$ alkenyl, $C_{2-4}$ alkynyl, $NO_2$, —CN, $OR^a$, $NR^a_2$, $COR^a$, $CO_2R^a$, and $CONR^a_2$; p is selected from 0, 1, 2, 3, and 4; m+n is selected from 0, 1, and 2.

In preferred embodiments, alkyls comprise the radical of saturated aliphatic groups, including straight-chain alkyl groups, and branched-chain alkyl groups. Alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, preferably 20 or fewer, and preferably 4 or fewer.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate.

Other examples of substitutes include any one or any combination of the following substituents: hydroxy, halogen, carboxyl, cyano, nitro, oxo (=O), thio (=S), methyl, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$, —NR$^x$C(S)R$^y$, —NR$^x$C(S)NR$^y$R$^z$, —SONR$^x$R$^y$, —SO$_2$NR$^x$R$^y$, —OR$^x$, —OR$^x$C(O)NR$^y$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^y$, —R$^x$OC(O)R$^y$, —SR$^x$, —SOR$^x$, —SO$_2$R$^x$, and —ONO$_2$, wherein R$^x$, R$^y$ and R$^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring.

In other preferred embodiments, alkyls also includes unsaturated aliphatic groups analogous in length and possible substitution to the alkyls described above, but that contain at least one double or triple bond respectively. An alkylaryl moiety is an alkyl substituted with an aryl (e.g., phenylmethyl (benzyl)). Aralkyl groups may be optionally substituted, either on the aryl portion of the aralkyl group or on the alkylene portion of the aralkyl group, with one or more substituents.

In another preferred embodiment, alkenyls and alkynyls comprise unsaturated aliphatic groups analogous in length and substitution to the alkyls described above. In certain aspects the molecules comprise at least one double or triple bond, respectively. For example, the invention contemplates cyano and alkynyl groups.

Aryl comprises the radical of aryl groups, including 5- and 6-membered single-ring aromatic groups that may include from zero to four heteroatoms (heteroaryl), for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like.

Those aryl groups having heteroatoms in the ring structure may also be referred to as "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, halogenated alkyl (including trifluoromethyl, difluoromethyl and fluoromethyl), halogenated alkoxy (including trifluoromethoxy, difluoromethoxy and fluoromethoxy), cyano, azido, heterocyclyl, alkylaryl, arylalkyl or an aromatic or heteroaromatic moiety. Aryl groups can also be fused or bridged with alicyclic or heterocyclic rings which are not aromatic so as to form a polycycle (e.g., tetralin).

In another preferred embodiment, the one or more compositions comprising: HSCl1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin); ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 ChemDiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573 HSCI1_000305, ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, PK04_097175, variants, analogs, isomers, salts and substituents thereof, inhibit GALK activity by at least about 50% as compared to controls. The inhibitory activity is further compared to a normal control (i.e. one who does not suffer from or predisposed to galactosemia and disorders thereof).

In a preferred embodiment, the one or more compositions comprising: HSCI1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin); ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 ChemDiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573, HSCI1_000305 (NF279), ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175 variants, analogs, isomers, salts and substituents thereof, inhibit GALK activity by at least about 75% as compared to a patient's original levels of GALK activity. The inhibitory activity is further compared to a normal control (i.e. one who does not suffer from or predisposed to galactosemia and disorders thereof).

In a preferred embodiment, the one or more compositions comprising: HSCI1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin);

ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 ChemDiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573, HSCI1_000305 (NF279), ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175 variants, analogs, isomers, salts and substituents thereof, inhibit GALK activity in a patient or cell by at least about 99% as compared to a patient's original levels of GALK activity or as compared to a normal cell. The inhibitory activity is further compared to a normal control (i.e. one who does not suffer from or predisposed to galactosemia and disorders thereof).

In a preferred embodiment, the one or more compositions comprising: HSCI1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin); ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 ChemDiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573, HSCI1_000305 (NF279), ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175 variants, analogs, isomers, salts and substituents thereof, inhibit GALK activity by 100% as compared to a patient's original levels of GALK activity or as compared to a normal cell.

The inhibitory activity can also be compared to a normal control (i.e. one who does not suffer from or predisposed to galactosemia and disorders thereof).

In another preferred embodiment, the compounds comprise HSCI1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin); ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 ChemDiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573, HSCI1_000305 (NF279), ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175 variants, analogs, isomers, salts and substituents thereof, inhibit one or more kinases as compared to a normal patient or normal cell by at least about 10%. Examples include, but not limited to the superfamily of small molecule kinases, also known as the GHMP (Galactose, Homoserine, Mevalonic acid, Phosphomevalonic acid) kinases. Examples within this superfamily include, but not limited to: galactokinase, homoserine kinase, mevalonate kinase, phosphomevalonate kinase, CDP-ME kinase, N-acetylgalactosamine kinase, mevalonate 5-diphosphate decarboxylase, and arabinose kinase. Other superfamilies and kinases that are comprised within these superfamilies are within the scope of the invention. Examples of superfamilies and other kinases include, but not limited to: nucleoside monophosphate (NMP) kinase; WNK kinases; MAPK (mitogen-activated protein kinase) super-family which is composed of three major sets of kinases: the extracellular-receptor kinases (ERK) include ERK1; ERK2; ERK3/ERK4, ERK5, and two types of MAPK-related kinases that respond to cellular stress and inflammatory signal: the c-Jun N-terminal kinases/stress-activated protein kinases (JNK/SAPK) which include JNK1, JNK2 and JNK3 and the p38 MAPKinases: p38alpha, p38beta2, p38gamma and p38delta.

Other kinases and families thereof can be screened for candidate kinase inhibitors using the methods described herein.

The compounds can be used in conjunction with one or more other compounds, both known or others identified using the high throughput screening assay described herein.

In another preferred embodiment, the compounds inhibit one or more kinases as compared to a normal patient or normal cell by at least about 50%. Examples of kinases include, but not limited to the superfamily of small molecule kinases, also known as the GHMP (Galactose, Homoserine, Mevalonic acid, Phosphomevalonic acid) kinases. Examples within this superfamily include, but not limited to: galactokinase, homoserine kinase, mevalonate kinase, phosphomevalonate kinase, CDP-ME kinase, N-acetylgalactosamine kinase, mevalonate 5-diphosphate decarboxylase, and arabinose kinase. Other superfamilies and kinases that are comprised within these superfamilies are within the scope of the invention. Examples of superfamilies and other kinases include, but not limited to nucleoside monophosphate (NMP) kinase; WNK kinases; MAPK (mitogen-activated protein kinase) super-family which is composed of three major sets of kinases: the extracellular-receptor kinases (ERK) include ERK1; ERK2; ERK3/ERK4, ERK5, and two types of MAPK-related kinases that respond to cellular stress and inflammatory signal: the c-Jun N-terminal kinases/stress-activated protein kinases (JNK/SAPK) which include JNK1, JNK2 and JNK3 and the p38 MAPKinases: p38alpha, p38beta2, p38gamma and p38delta.

Other kinases and families thereof can be screened for candidate kinase inhibitors using the methods described herein.

In another preferred embodiment, the compounds modulate biochemical pathways in cells or in vivo by acting as modulators of enzymes. The modulation of enzymes in pathways by the compounds of the invention preferably target one or more reactions in the pathway. For example, the N-acetyl-galactosamine kinase is an important enzyme in glycosylation reactions. Thus, a modulator of this enzyme will affect cellular glycan production. In another example, the arabinose kinase enzyme is implicated in arabinose metabolism. Further, the 4-Diphosphocytidyl-2C-methyl-D-erythritol (CDP-ME) kinase is involved in isoprenoid biosynthesis in microbes, including bacteria and protozoa.

In another preferred embodiment, the compounds comprise: HSCI1_000333 Calbiochem 540215 (Tyrosine Phosphatase CD45 inhibitor); K04_097174 582836 Neumann; TimTec1_006661TimTec ST4094742; HSCI1_000182 Calbiochem 428022 (β-Lapachone); ChemDiv3_007091 ChemDiv 7218-1573; ChemDiv3_000368 ChemDiv 1184-1682; TimTec1_001881 TimTec ST026634; ChemDiv3_002016 ChemDiv 3553-1484; SPBio_001210 (Hexachlorophene); SMP2_000049 Sigma E9259 (Erythrosin B); ChemDiv3_007133 ChemDiv 7218-1483; TimTec1_001324 TimTec ST014236; ChemDiv3_007089 ChemDiv 7218-1459; Maybridge4_001932 JFD03061; TimTec1_000233 TimTec ST000572; ChemDiv3_014119 ChemDiv 7218-1576; ChemDiv3_001694 ChemDiv 3241-0272; SPBio_000126 Spectrum2_000113 (Bithionol); SPBio_001697 Spectrum2_001629 (Rhodomyrtoxin); ChemDiv3_002334 ChemDiv 3696-0201; ChemDiv3_000903 ChemDiv 1887-0088; TimTec1_001108 TimTec ST014268; Maybridge4_001288 HTS01859; SMP2_000320 Sigma S1014 (Streptonigrin); TimTec1_001055 TimTec ST012305; ChemDiv3_001508 ChemDiv 3229-1543; ChemDiv3_007160 ChemDiv 8012-2663; ChemDiv3_001677 ChemDiv 3062-0036; TimTec1_003525 TimTec ST048025; BiomolKI2_000062 BiomolEI-307; ChemDiv3_001693 ChemDiv 3175-0337; TimTec1_002320 TimTec ST032682; ChemDiv3_003365 ChemDiv 4456-1104; TimTec1_005567 TimTec ST4029573, HSCI1_000305 (NF279), ChemDiv3_002459, HSCI1_000035, PK04_097255, PK04_098179, SCI1_000331, HSCI1_000187, Maybridge4_003162, ACon1_002474, Maybridge4_002460, HSCI1_000002, ACon1_001911, SMP2_000091, ChemDiv3_006723, ChemDiv3_000237, PK04_097046, PK04_097081, HSCI1_000004, ChemDiv3_015769, PK04_097057, TimTec1_000037, SPBio_000035, PK04_098125, SPBio_000341, PK04_097018, HSCI1_000315, PK04_097253, ChemDiv3_014394, SPBio_000394, SPBio_000649, ChemDiv3_001455, ChemDiv3_003258, ChemDiv3_002419, PK04_097003, ChemDiv3_000127, ACon1_001054, ChemDiv3_000428, Maybridge4_000719, PK04_097149, PK04_097012, PK04_097295, Maybridge4_000547, Maybridge4_000383, HSCI1_000319, ChemDiv3_012072, SPBio_000927, SPBio_000031, HSCI1_000222, PK04_098045, ChemDiv3_011472, Maybridge4_000280, HSCI1_000113, TimTec1_002292, SPBio_000029, Maybridge4_000025, SPBio_000260, TimTec1_006170, HSCI1_000274, PK04_098207, SPBio_001687, ChemDiv3_000631, SPBio_000023, PK04_097102, Maybridge4_001879, SPBio_002863, ChemDiv3_012460, ChemDiv3_014894, Maybridge4_002594, HSCI1_000296, PK04_098211, ChemDiv3_014798, SPBio_001777, HSCI1_000387, HSCI1_000078, PK04_097298, PK04_098190, ChemDiv3_000384, PK04_097016, ACon1_001710, PK04_097049, TimTec1_001159, TimTec1_001097, SPBio_000420, ICCB6_000340, HSCI1_000133, HSCI1_000357, TimTec1_001160, Maybridge4_003860, HSCI1_000306, TimTec1_005643, TimTec1_000797, ACon1_002102, ChemDiv3_006929, PK04_098021, ChemDiv3_007117, SPBio_000585, Maybridge4_004121, PK04_097115, TimTec1_006683, ChemDiv3_000908, HSCI1_000235, HSCI1_000115, HSCI1_000198, ChemDiv3_014504, PK04_098163, PK04_098082, BiomolKI2_000009, PK04_098199, ChemDiv3_011481, PK04_097282, HSCI1_000048, PK04_097194, HSCI1_000332, ChemDiv3_005246, PK04_097319, TimTec1_004971, HSCI1_000249, ChemDiv3_004096, ChemDiv3_008579, HSCI1_000346, PK04_097275, PK04_097009, ChemDiv3_004268, Maybridge4_000651, HSCI1_000020, PK04_096001, PK04_097317, ChemDiv3_014350, ChemDiv3_000637, HSCI1_000294, ChemDiv3_007090, Maybridge4_001879, HSCI1_000185, ACon1_001657, BiomolKI2_000004, SPBio_000589, PK04_098003, PK04_130094, ChemDiv3_016344, ICCB6_000298, ChemDiv3_004352, SMP2_000306, PK04_097293, ChemDiv3_001801, ChemDiv3_012486, HSCI1_000032, TimTec1_002520, Maybridge4_001966, ChemDiv3_014059, PK04_130132, ICCB6_000268, ACon1_000576, ChemDiv3_014037, ChemDiv3_016150, BiomolKI2_000036, ChemDiv3_007069, HSCI1_000103, HSCI1_000036, HSCI1_000183, ChemDiv3_002888, PK04_098180, SPBio_000230, PK04_097256, Maybridge4_000309, BiomolKI2_000043, ChemDiv3_000369, PK04_097173, HSCI1_000304, ACon1_001926, ChemDiv3_011138, ChemDiv3_005090, TimTec1_006662, ChemDiv3_011895, Maybridge4_003457, and PK04_097175, variants, analogs, isomers, salts and substituents thereof, inhibit one or more kinases as compared to a normal patient or normal cell by at least about 90%. Examples include, but not limited to the superfamily of small molecule kinases, also known as the GHMP (Galactose, Homoserine, Mevalonic acid, Phosphomevalonic acid) kinases. Examples within this superfamily include, but not limited to: galactokinase, homoserine kinase, mevalonate kinase, phosphomevalonate kinase, CDP-ME kinase, N-acetylgalactosamine kinase, mevalonate 5-diphosphate decarboxylase, and arabinose kinase. Other superfamilies and kinases that are comprised within these superfamilies are within the scope of the invention. Examples of superfamilies and other kinases include, but not limited to: nucleoside monophosphate (NMP) kinase; WNK kinases; MAPK (mitogen-activated protein kinase) super-family which is composed of three major sets of kinases: the extracellular-receptor kinases (ERK) include ERK1; ERK2; ERK3/ERK4, ERK5, and two types of MAPK-related kinases that respond to cellular stress and inflammatory signal: the c-Jun N-terminal kinases/stress-activated protein kinases (JNK/SAPK) which include JNK1, JNK2 and JNK3 and the p38 MAPKinases: p38alpha, p38beta2, p38gamma and p38delta.

Other kinases and families thereof can be screened for candidate kinase inhibitors using the methods described herein.

Administration of Compositions to Patients

The compositions or agents identified by the methods described herein may be administered to animals including human beings in any suitable formulation. For example, the compositions for inhibiting GALK activity may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions. The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

Formulations

While it is possible for a composition to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Identification of Further Candidate Therapeutic Agents

In a preferred embodiment, the high-throughput screening assay (HTS) screening assay is used to screen a diverse library of member compounds. The "compounds" or "candidate therapeutic agents" or "candidate agents" can be any organic, inorganic, small molecule, protein, antibody, aptamer, nucleic acid molecule, or synthetic compound.

In another preferred embodiment, the candidate agents modulate enzymes. These enzymes can be involved in various biochemical pathways such as synthetic pathways, breakdown pathways, e.g. ubiquitin, enzymatic pathways, protein trafficking pathways, metabolic pathways, signal transduction pathways, and the like. These pathways include prokaryotic and eukaryotic pathways.

In another preferred embodiment, the high throughput assays identifies candidate agents that target and modulate bacterial pathways. The candidate agents would be useful in developing and identifying novel antibiotic or other antimicrobial agents.

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA*. 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and nonpeptide lead discovery using robotically synthesized soluble libraries, *Can J. Physiol Pharmacol.* 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci.* USA, 90:6909-6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261: 1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569, 588); thiazolidinones and metathiazanones (U.S. Pat. No. 5,549,974); pyrrolidines (U.S. Pat. Nos. 5,525,735 and 5,519, 134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

Small Molecules: Small molecule test compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czamik, *Curr.*

*Opin. Chem. Bio.,* 1:60 (1997). In addition, a number of small molecule libraries are commercially available.

As discussed above if there is ample GALK activity, ATP will be used up in step 1 and little will be left for the luciferase reaction in step 2 of the high throughput screening assay. Consequently, the more active GALK reaction, the less luminescence will be recorded. The luciferase contained in the Kinase-Glo® is formulated to generate a stable "glow-type" luminescent signal that has a half-life greater than 4 hours.

The whole procedure can be fully automated. For example, sampling of sample materials may be accomplished with a plurality of steps, which include withdrawing a sample from a sample container and delivering at least a portion of the withdrawn sample to test platform. Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns," rectangular arrays with "n-rows" by "m-columns," round arrays, triangular arrays with "r-" by "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

According to the present invention, one or more systems, methods or both are used to identify a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Generally, the automated system includes a suitable protocol design and execution software that can be programmed with information such as synthesis, composition, location information or other information related to a library of materials positioned with respect to a substrate. The protocol design and execution software is typically in communication with robot control software for controlling a robot or other automated apparatus or system. The protocol design and execution software is also in communication with data acquisition hardware/software for collecting data from response measuring hardware. Once the data is collected in the database, analytical software may be used to analyze the data, and more specifically, to determine properties of the candidate drugs, or the data may be analyzed manually.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Embodiments of inventive compositions and methods are illustrated in the following examples. These examples are provided for illustrative purposes and are not considered limitations on the scope of inventive compositions and methods.

Materials and Methods

Over-Expression and Purification of Human Galactokinase (GALK)

cDNA coding for the human GALK1 gene was obtained from the I.M.A.G.E. consortium (Clone ID: 3501788). This sequence was amplified by PCR using specific primers designed to introduce a NcoI restriction site and a His6 epitope tag at the 5' end, as well as a 3' NdeI restriction site. The resulting fragment was then sub-cloned into plasmid pET15b (Novagen) using the NcoI and NdeI cloning sites. The nucleotide sequence of the GALK cDNA insert was confirmed by DNA sequencing using the T7 forward and reverse primers (Novagen). Subsequently, the plasmid containing the designed insert was transformed into *Escherichia coli* HMS174 (DE3) (Novagen) cells. Isopropyl β-D-1-thiogalactopyranoside (IPTG, 1 mM final concentration) was added to cell culture in LBAmp on reaching OD600=0.6 at 37° C. to induce over-expression of GALK for 3 hrs, and the pellet subsequently stored at −80° C.

Protein purification was conducted at 4° C. throughout. Briefly, cell pellets were resuspended in lysis buffer (50 mM $NaH_2PO_4$, 300 mM NaCl, 10 mM imidazole, and 100 mM galactose, pH=8). Cells were then lysed using a microfluidizer and clarified by centrifugation. Lysate was loaded onto a chromatography column containing Nickel affinity resin. The resin was washed and bound GALK was eluted using an imidazole concentration gradient. Final purified GALK was concentrated to 1 mg/mL, dialyzed into PBS, aliquoted and stored frozen at −80° C. Galactose-dependent ATPase activity was verified using the standard pyruvate kinase/lactate dehydrogenase-coupled assay (Platt, A., et al., *Proc Natl Acad Sci USA*, 2000, 97(7): p. 3154-9).

Development of High-Throughput Screening Assay for GALK

Using the Kinase-Glo™ reagent (Promega, Madison, Wis.), a miniaturized, two-step HTS assay for GALK was developed. This assay measures GALK activity indirectly by determining the amount of ATP remained after completion of the GALK-mediated reaction (step 1): Galactose+ATP→gal-1-p+ADP. If there is ample GALK activity, most ATP will be used up in step 1 and little will be left for the luciferase reaction in step 2: ATP+Luciferin & Luciferase (Kinase Glo™)→oxyluciferin+light. Consequently, the more active GALK reaction, the less luminescence will be recorded.

Final assay conditions in a total volume 30 μL were as follows: 0.15 μg/30 μL GALK, 5 mM $MgCl_2$, 60 mM NaCl, 20 mM HEPES, 1 mM DTT, 0.5% DMSO, 0.01% BSA, 1 mM galactose, and 5 μM ATP. After 60 minutes at room temperature (22° C.), 30 μL of Kinase Glo™ (Promega) was added, and luminescence was measured within 30 min using an Envision Multilabel Plate Reader (Perkin Elmer).

Z' factor for the assays with GALK (samples) and assays without GALK (controls), was determined using the formula Z' factor=$1-[3\times(\sigma_p+\sigma_n)/|\mu_p-\mu_n|]$. The term $|\mu_p-\mu_n|$ denotes the absolute difference between the mean of the samples and the mean of the controls, whereas $\sigma_p$ and $\sigma_n$ correspond to standard deviations for the samples and controls respectively. As a proof of principle, we used the ATP analog adenosine 5'-O-(3-thio-) triphosphate (ATP-γ-S), to demonstrate increasing inhibition of GALK when increasing ATP-γ-S from 0 to 13.3 μM, keeping ATP constant at 5 μM.

High-Throughput Screening of Small Molecule Inhibitors of GALK

In the course of 12 days, nearly 50,000 compounds from various libraries of small molecules with diverse structural scaffolds were screened for their inhibitory properties of GALK activity in vitro. Briefly, 100 nL of a solution of compounds dissolved in DMSO at a concentration of 10 mM was pinned, using CyBi™ Well 384/1536 (CyBio, Inc., Woburn, Mass.), into 384-well plates containing 20 μL of Master Mix #1 (0.015 μg GALK, 5 mM $MgCl_2$, 60 mM NaCl, 20 mM HEPES, 1 mM DTT, and 0.01% BSA). After allowing the single compound to equilibrate with GALK for 60 min, the GALK reaction was started by adding 10 μL of Master Mix #2 (5 mM $MgCl_2$, 60 mM NaCl, 20 mM HEPES, 1 mM DTT, 3 mM α-D-galactose, 0.01% BSA, and 15 μM ATP). The reaction was then allowed to proceed at room temperature (22° C.) for 60 min. Then, 30 μL of Kinase-Glo™ was added to stop the reaction, and luminescence was measured 15 to 30 min later using the Envision Multilabel Plate Reader (PerkinElmer). 50,000 small molecules were screened, in duplicate, for inhibitory properties against purified GALK. The Z' factor assay was included each day as part of the quality control process.

Data Analysis:

Raw data were submitted to the data analysis team of the HTS facility for further analysis. In short, duplicate luminescence measurements were corrected for background measurements using the method described by Seiler et al. (*Nucl. Acids Res* 2007). For each compound, the cosine correlation of the duplicate pair (A and B) of dimensionless z-score values yielded a composite z-score value representing the final primary screening result. Reproducibility of the 2 z-scores was defined as the cosine of the replicate vector [z-scoreA, z-scoreB] and the vector [1, 1] representing perfect reproducibility.

$IC_{50}$ Determination

As the percentage of substrate conversion can have significant impact on the accuracy of IC50 determination, the preferred approach is to determine reaction rates at initial velocity (i.e., zero substrate conversion). Initially, the $IC_{50}$ was determined with the luminescence-based assay, it was found that the percentages of substrate conversion were relatively high (~50%). The dose response of the selected compounds was analyzed using the standard pyruvate kinase/lactate dehydrogenase-coupled assay (Heinrich M R, Howard S M: Galactokinase. *Methods Enzymol* 1966; 9:407-412). In this assay, the amount of galactose present in the reaction is kept in excess, whereas ATP consumed by the galactokinase reaction is recycled by the pyruvate kinase reaction. As a result, the reaction rates calculated will be close to initial velocity. $IC_{50}$ values were determined on normalized data from this enzyme-linked assay using the values obtained for the corresponding controls (no inhibitor) as 100%. These data were fitted with a standard dose response inhibition model using GraphPad Prism 5.01 software (San Diego, Calif.), and a log(inhibitor) versus normalized response model, y=100/[1+ $10^{(x-logIC50)}$], was established for each inhibitor. The models demonstrated adequate fit, with $R^2$ values of all curves greater than 0.90.

Example 1

High-Throughput Screening Assay (HTS)

The two main objectives were the development of a robust high-throughput screening (HTS) assay for human galactokinase (GALK) activity, activity of other kinases, and the use of this assay to identify small molecules that inhibited human GALK activity in vitro. The latter has significant implications in treating chronic complications suffered by patients with Classic Galactosemia. Moreover, being the first enzyme of the Leloir pathway of galactose metabolism, the level of GALK activity dictates the amount of galactose entry into the galactose metabolic pathway, making GALK a significant biological target for overall galactose metabolism. Discovery of inhibitors for this important biological target and other targets, such as, for example, galactokinase, homoserine kinase, mevalonate kinase, phosphomevalonate kinase, CDP-ME kinase, N-acetylgalactosamine kinase, mevalonate 5-diphosphate decarboxylase, and arabinose kinase, can be achieved by this assay and will advance the understanding of the role played by galactose catabolism in cellular metabolism.

Results and Discussion

Overexpression and purification of human galactokinase cDNA coding for the human GALK1 gene was obtained from the I.M.A.G.E. consortium (Clone ID: 3501788). This sequence was amplified by PCR using specific primers designed to introduce an NcoI restriction site and an His6 epitope, tag at the 5' end, as well as a 3' BamHI restriction site. The resulting fragment was then subcloned into plasmid pET15b (Novagen, Madison, Wis.) using the NcoI and BamHI cloning sites. The nucleotide sequence of the GALK1 cDNA insert was confirmed by DNA sequencing using the T7 forward and reverse primers (Novagen). Subsequently, the plasmid containing the designed-insert was transformed into *Escherichia coli* HMS174 (DE3) (Novagen) cells. Isopropyl β-D-1-thiogalactopyranoside (IPTG) was added at a final concentration of 1 mM to cell culture in LBAmp upon reaching $OD_{600}=0.6$ at 37° C. to induce overexpression of GALK for 3 h, and the pellet was subsequently stored at −80° C.

Protein purification was conducted at 4° C. throughout. Briefly, cell pellets were resuspended in lysis buffer (50 mM $NaH_2PO_4$, 300 mM NaCl, 10 mM imidazole, and 100 mM galactose, pH 8). Cells were then lysed using a microfluidizer and clarified by centrifugation, and the lysate was loaded onto a chromatography column containing Nickel affinity resin. The resin was washed, and bound GALK was eluted using an imidazole concentration gradient. Final purified GALK was concentrated to 1 mg/mL, dialyzed into phosphate-buffered saline (PBS), aliquoted, and stored frozen at −80° C. Galactose-dependent adenosine triphosphatase (ATPase) activity was verified using the standard pyruvate kinase/lactate dehydrogenase-coupled assay.

Development of High-Throughput Screening Assay for GALK:

Using the Kinase-Glo™ reagent (Promega, Madison, Wis.), a miniaturized, 2-step HTS assay for GALK was developed. This assay measured GALK activity indirectly by determining the amount of adenosine triphosphate (ATP) remaining after completion of the GALK-mediated reaction (step 1): galactose+ATP→gal-1-p+adenosine diphosphate (ADP). If there is ample GALK activity, most ATP is used up in step 1, and little is left for the luciferase reaction (step 2): ATP+luciferin and luciferase (Kinase-Glo™)→oxyluciferin+light.

Final assay conditions in a total volume of 30 µL were as follows: 0:15 µg GALK, 5 mM $MgCl_2$, 60 mM NaCl, 20 mM HEPES, 1 mM dithiothreitol (DTT), 0.5% DMSO, 0.01% bovine serum albumin (BSA), 1 mM α-D-galactose, and 5 µM ATP. After 60 min at room temperature (22° C.), 30 µL of Kinase-Glo™ was added, and luminescence was measured within 30 min using an Envision Multilabel Plate Reader (PerkinElmer, Waltham, Mass.). The Wellmate® reagent dispenser (Matrix Technologies, Hudson, N.H.) was used to dispense biochemicals and Kinase-Glo™.

Z' factor for the assays with GALK (samples) and assays without GALK (controls) was determined using the following formula: Z' factor=$1-[3\times(\sigma_p+\sigma_n)/|\mu_p-\mu_n|]$. The term $|\mu_p-\sigma_n|$ denotes the absolute difference between the mean of the samples and the mean of the controls, whereas $\sigma_p$ and $\sigma_n$ correspond to standard deviations for the samples and controls, respectively.

As a proof of principle, the ATP analog adenosine 5'-O-(3-thio-)triphosphate (ATP-γ-S) was used to demonstrate increasing inhibition of GALK when increasing ATP-γ-S from 0 to 13.3 µM, keeping ATP constant at 5 µM.

HTS of Small-Molecule Inhibitors of GALK:

Using the same expression system, sufficient GALK enzyme was harvested from 200 liters of bacterial culture and the GALK enzyme purified had high specific activity. Therefore, only 0.015 µg of GALK protein per well was used in each screening assay. Fifty thousand (50,000) compounds from various libraries of small molecules with diverse structural scaffolds were screened for inhibitory properties of GALK activity in vitro. Briefly, 100 mL of a solution of compounds dissolved in DMSO at a concentration of 10 mM was pinned, using CyBi™ Well 384/1536 (CyBio, Inc., Woburn, Mass.), into 384-well plates containing 20 µL of Master Mix #1 (0.015 µg GALK, 5 mM $MgCl_2$, 60 mM NaCl, 20 mM HEPES, 1 mM DTT, and 0.01% BSA). After allowing the single compound to equilibrate with GALK for 60 min, the GALK reaction was started by adding 10 µL of Master Mix #2 (5 mM $MgCl_2$, 60 mM NaCl, 20 mM HEPES, 1 mM DTT, 3 mM α-D-galactose, 0.01% BSA, and 15 µM ATP). The reaction was then allowed to proceed at room temperature (22° C.) for 60 min. Then, 30 µl of Kinase-Glo™ was added to stop the reaction, and luminescence was measured 15 to 30 min later using the Envision Multilabel Plate Reader (PerkinElmer). 50,000 small molecules were screened, in duplicate, for inhibitory properties against purified GALK. The Z' factor assay was included each day as part of the quality control process.

Data Analysis:

Raw data were submitted to the data analysis team of the HTS facility for further analysis. In short, duplicate luminescence measurements were corrected for background measurements using the method described by Seiler et al. (ChemBank: a small-molecule screening and cheminformatics resource database. *Nucleic Acids Res* 2007). For each compound, the cosine correlation of the duplicate pair (A and B) of dimensionless z-score values yielded a composite z-score value representing the final primary screening result as previously described. Reproducibility of the 2 z-scores was defined as the cosine of the replicate vector [z-scoreA, z-scoreB] and the vector [1, 1] representing perfect reproducibility. Details regarding the reproducibility score calculation can be found at the Chembank Web site (chembank.broad.harvard.edu).

$IC_{50}$ Determination:

As the percentage of substrate conversion can have significant impact on the accuracy of $IC_{50}$ determination, the preferred approach is to determine reaction rates at initial velocity (i.e., zero substrate conversion). Initially, when $IC_{50}$ was determined with the luminescence-based assay, it was found that the percentages of substrate conversion were relatively high (~50%). The dose response of the selected compounds was analyzed using the standard pyruvate kinase/lactate dehydrogenase-Coupled assay. In this assay, the amount of galactose present in the reaction was kept in excess, whereas ATP consumed by the galactokinase reaction was recycled by the pyruvate kinase reaction. As a result, the reaction rates calculated were close to initial velocity. $IC_{50}$ values were determined on normalized data from this enzyme-linked assay using the values obtained for the corresponding controls (no inhibitor) as 100%. These data were fitted with a standard dose response inhibition model using GraphPad Prism 5.01 software (San Diego, Calif.), and a log(inhibitor) versus normalized response model, $y=100/[1+10(x-logIC_{50})]$, was established for each inhibitor. The models demonstrated adequate fit, with $R^2$ values of all curves greater than 0.90.

Results and Discussion

Figure 2:
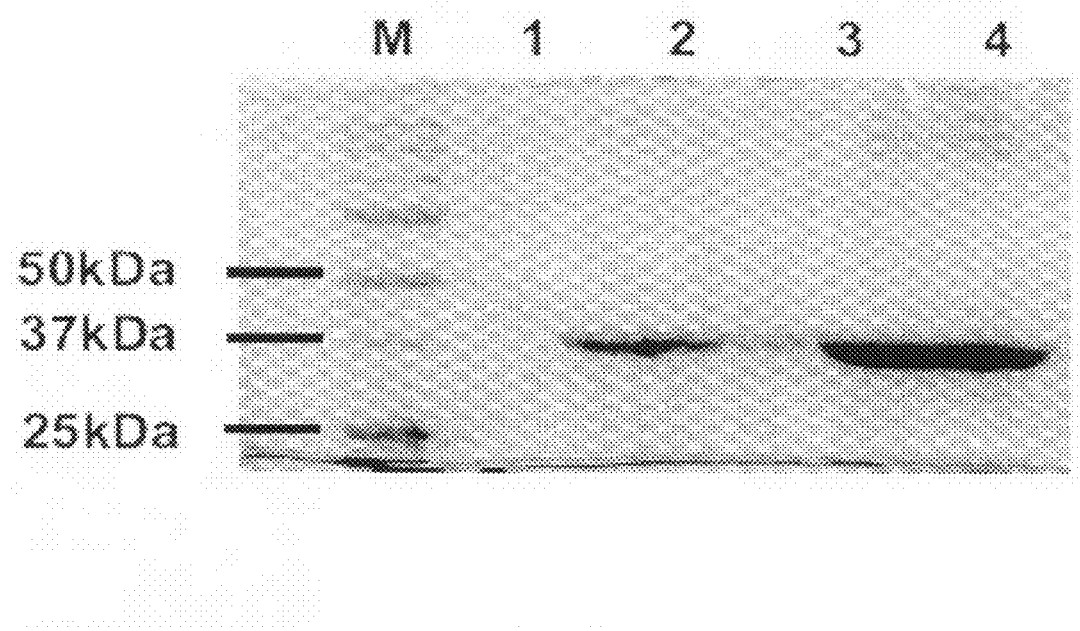
FIG. 2 is a scan of a photograph of a gel showing the purification of human GALK. Different amounts of $Ni^{2+}$-NTA affinity-purified GALK protein were loaded on sodium dodecyl sulfate-polyacrylamide gel electrophoresis (SD-SPAGE) as follows: M, molecular weight markers; 1, unloaded; 2, 1.25 μg GALK; 3, unloaded but some spillover of GALK from lane 4 was seen; 4, 6.25 μg GALK.

Over-expression and purification of human galactokinase (GALK): Initial estimation showed that a minimal of 5 mg (milligrams) of purified GALK would be required for the development of the HTS assay, as well as the subsequent screenings of 50,000 compounds in duplicates. Since overexpression and purification of active recombinant galactokinases had been successfully performed via affinity-chromatography using both *E. coli* and yeast as hosts (Thoden, J. B., et al., *J Biol Chem*, 2005. 280(10): p. 9662-70; Timson, D. J. and R. J. Reece. *Eur J Biochem*, 2003. 270(8): p. 1767-74), these protocols were adapted to prepare sufficient human GALK enzyme for the screening experiments. As shown in FIG. 2, a typical yield of 0.1 mg of purified GALK protein from one liter of bacterial culture was achieved. Galactose-dependent ATPase activity of the purified enzyme was verified using the standard pyruvate kinase/lactate dehydrogenase-coupled assay (Platt, A., et al., *Proc Natl Acad Sci USA*, 2000. 97(7): p. 3154-9). The presence of purified recombinant His6-tagged GALK protein was confirmed using anti-His6-tag antibody. Using the standard pyruvate kinase/lactate dehydrogenase-coupled assay, the $K_M$ was established for ATP at 42 µM, and $K_M$ for galactose was 210 µM in the purified human GALK.

Development of HTS assay for purified GALK: Despite the relatively low yield of GALK from the bacterial expression system, sufficient GALK enzyme was harvested to establish a high-throughput biochemical assay for GALK activity in a 384-well microplate format at the HTS facility at the Broad Institute. As described in Materials and Methods, the 2-step luminescence-based high-throughput assay measures GALK activity indirectly by quantifying the amount of ATP that remained in the GALK reaction. Therefore, the luminescent signal is inversely proportional to the amount of kinase activity.

Figure 3A:
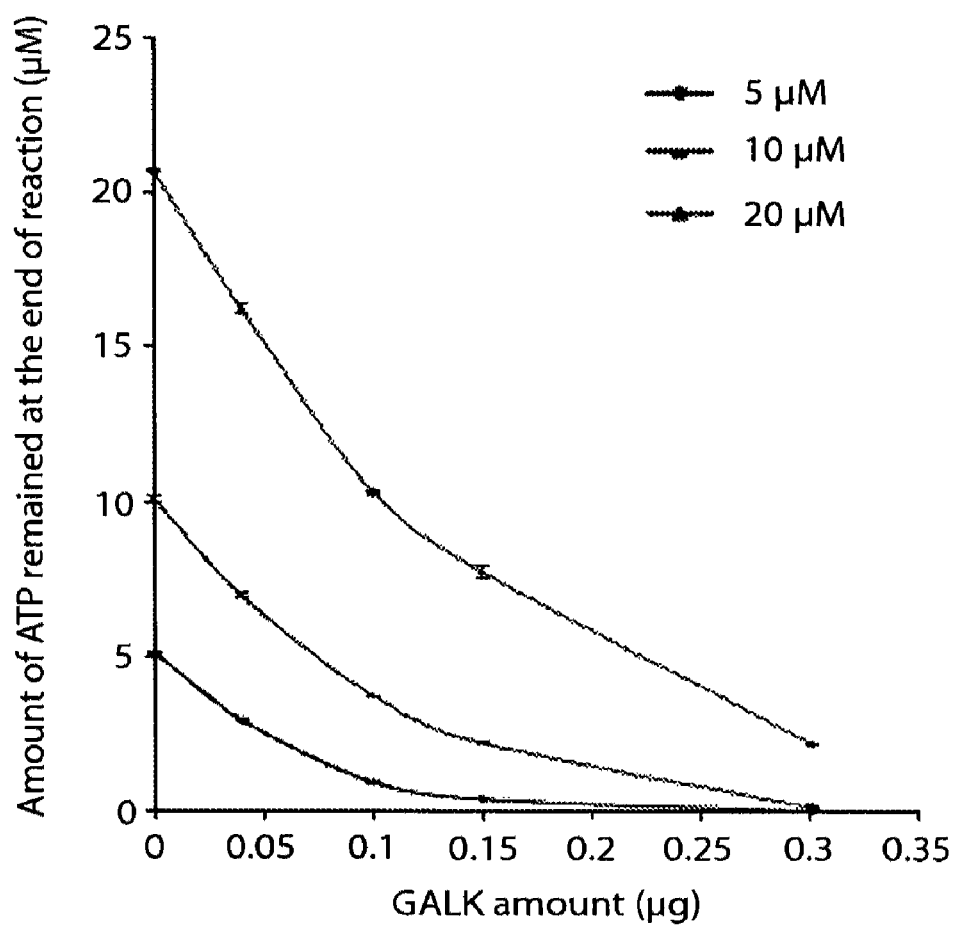
FIGS. 3A-3C are graphs showing Galactokinase (GALK) high-throughput screening (HTS) optimization.

During the assay development phase, the aim was to identify reaction conditions that would use the minimal amount of GALK enzyme, give a wide sensitivity range (i.e., high signal-to-noise ratio), and ensure that the reaction kinetics in the presence of a strong GALK inhibitor is within linear range. The largest signal-to-noise ratio achieved among all tested conditions was 96-fold, which took place with 0.15 µg GALK protein in the presence of 5 µM ATP over a time course of 60 min at room temperature (FIG. 3A). This signal-to-noise ratio indicated a good dynamic range, and this assay provided the optimal conditions to identify strong inhibitors of GALK.

Figure 3B:
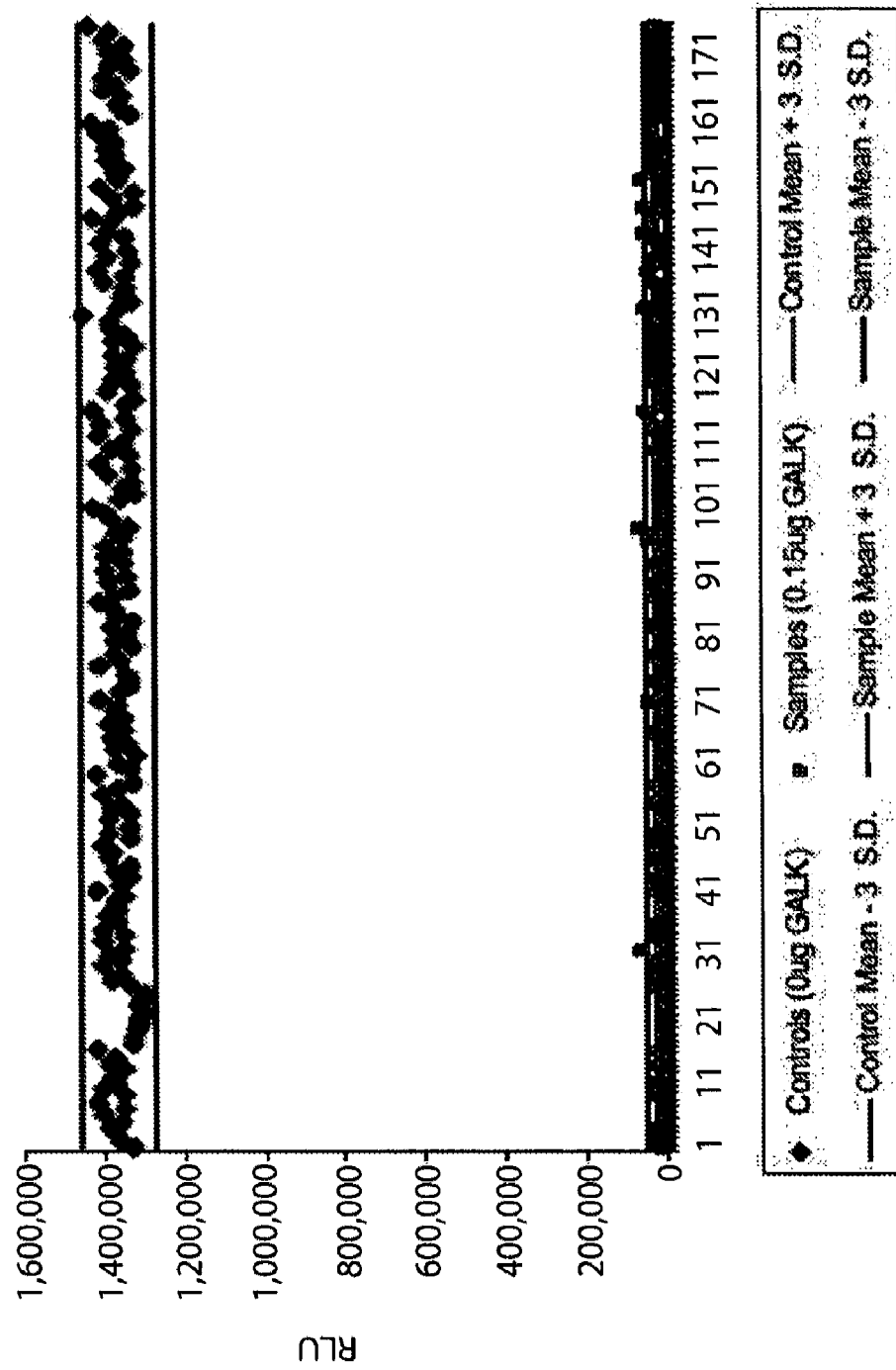
Figure 3C:
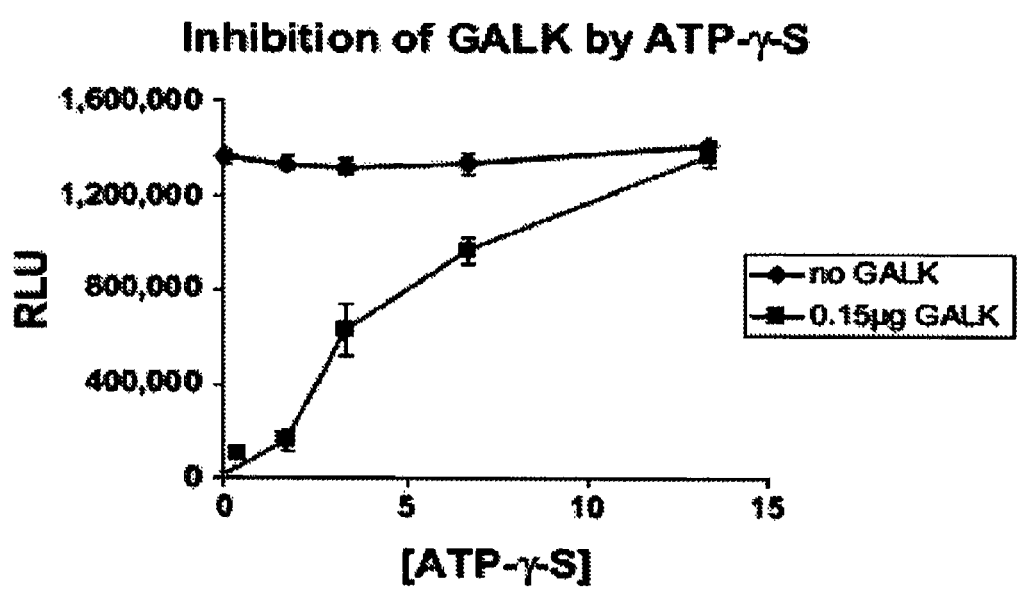

To test the robustness of the HTS assay, Z' factor analysis of the results was performed. As illustrated in FIG. 3B, a Z' factor of 0.91 was determined from the assay. Therefore, a very robust, miniaturized, 2-step in vitro HTS assay for recombinant human GALK was established. As a proof of concept, it was shown that an ATP mimetic, ATP-γ-S, acted as a GALK inhibitor by demonstrating decreased GALK activity in the presence of an increasing amount of ATP-γ-S (FIG. 3C).

It is noteworthy that the 2-step luminescence-based assay executed in this case measured the rate of disappearance of a substrate, rather than the formation of the product(s). The more luminescence detected at the endpoint, the less GALK activity was inferred. Although false negatives may be an undesirable outcome, those compounds are likely to be the less selective inhibitors that compete for ATP binding sites in other kinases. As a result, this assay reduces number of non-selective hits for GALK.

Figure 4:
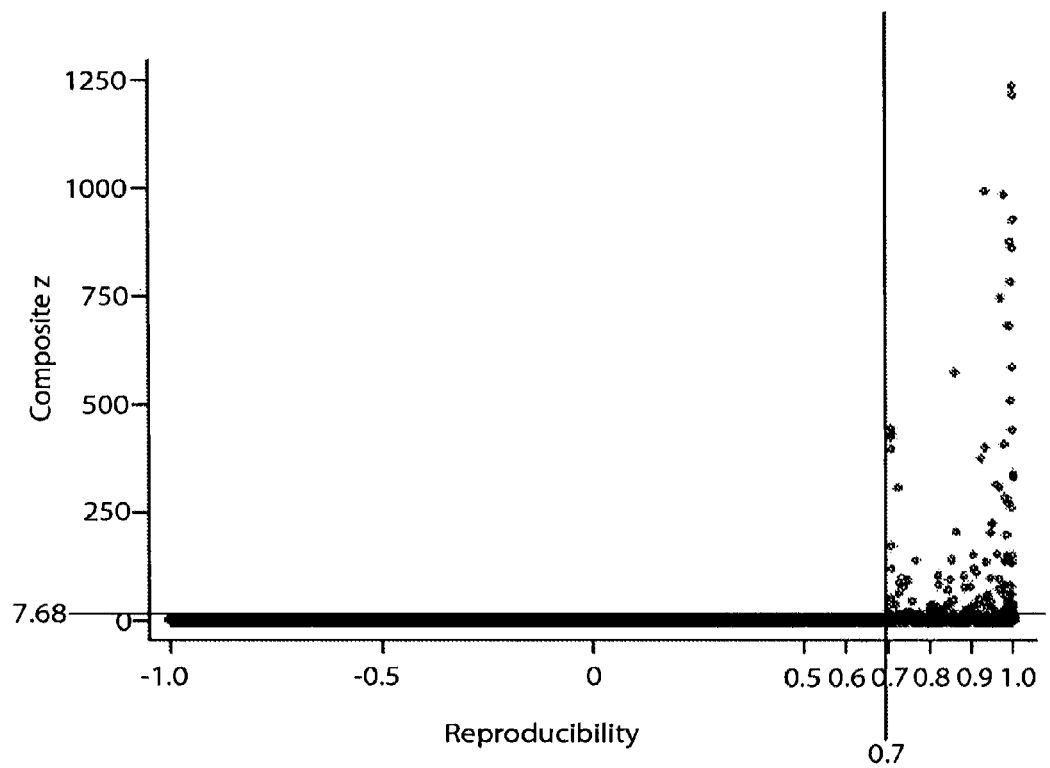
FIG. 4 is a graph showing the selection of 150 compounds from primary screen. A composite z-score and a reproducibility score were assigned to each of the 50,000 compounds tested based on their ability to inhibit galactokinase (GALK) activity in vitro and the reproducibility of the 2 replicate results. The 150 compounds with a reproducibility score above 0.70 and a composite z-score greater than 7.68 were selected.

HTS of small-molecule inhibitors of GALK: The final concentration of the compounds in the assay was in the micromolar range. A Z' factor assay was included each day as part of the quality control process, with a Z' factor of 0.9 or above observed throughout all screening days. From the standard curves constructed with varying amount of GALK, it was found that a composite z-score of 7.68 was equivalent to 86.3% inhibition of GALK activity. Hits were defined arbitrarily as a composite z-score above 7.68 in combination with a reproducibility score of at least 0.7 (FIG. 4). Based on these criteria, 200 compounds, representing 0.4% of the total 50,000 compounds in the libraries, were found to inhibit GALK activity by 86.3% or more. In total, 150 of the 200 compounds were subsequently selected for repeated testing (i.e., confirmatory screen) under identical experimental conditions. Most hits not selected for confirmatory screen were compounds with a molecular weight in excess of 500. As a validation of our screen, a few known kinase inhibitors were indentified among the hits, whereas most of the others are novel compounds that have not been characterized.

Figure 5:
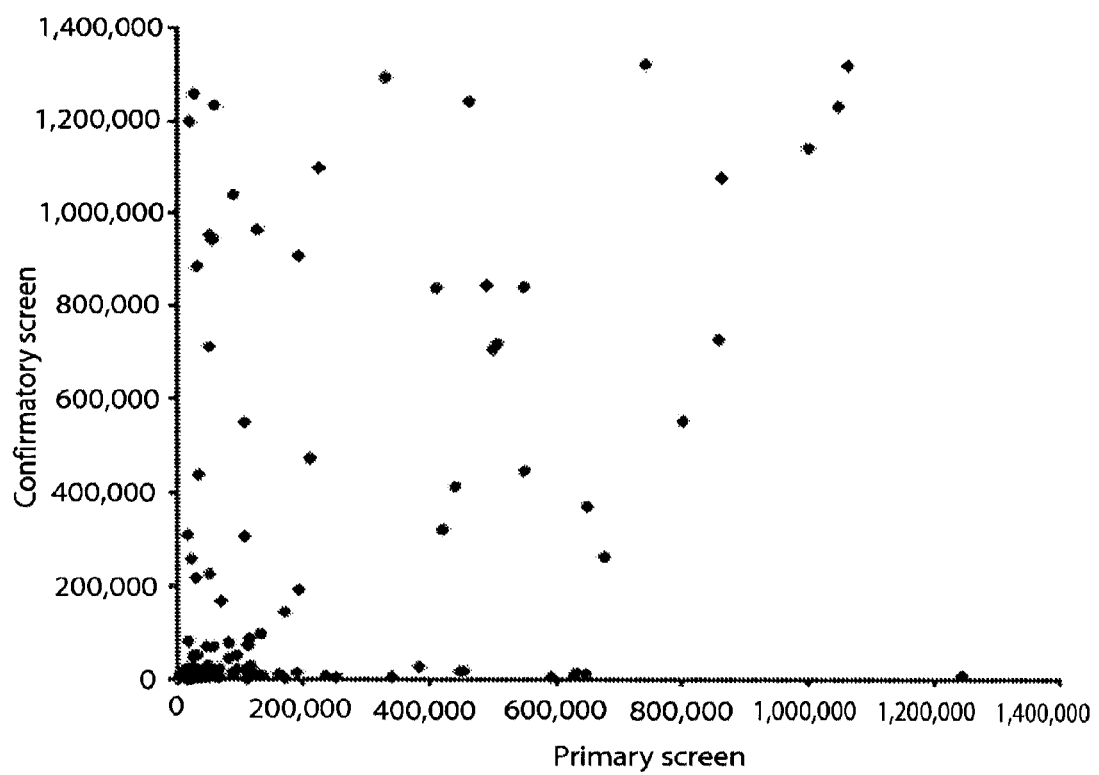
FIG. 5 is a graph showing the primary versus the secondary screen. Average (n=2) luminescence values recorded for the top 150 compounds selected from the primary screen were plotted against average (n=2) luminescence values of the corresponding compounds recorded at the confirmatory screen.
Figure 6:
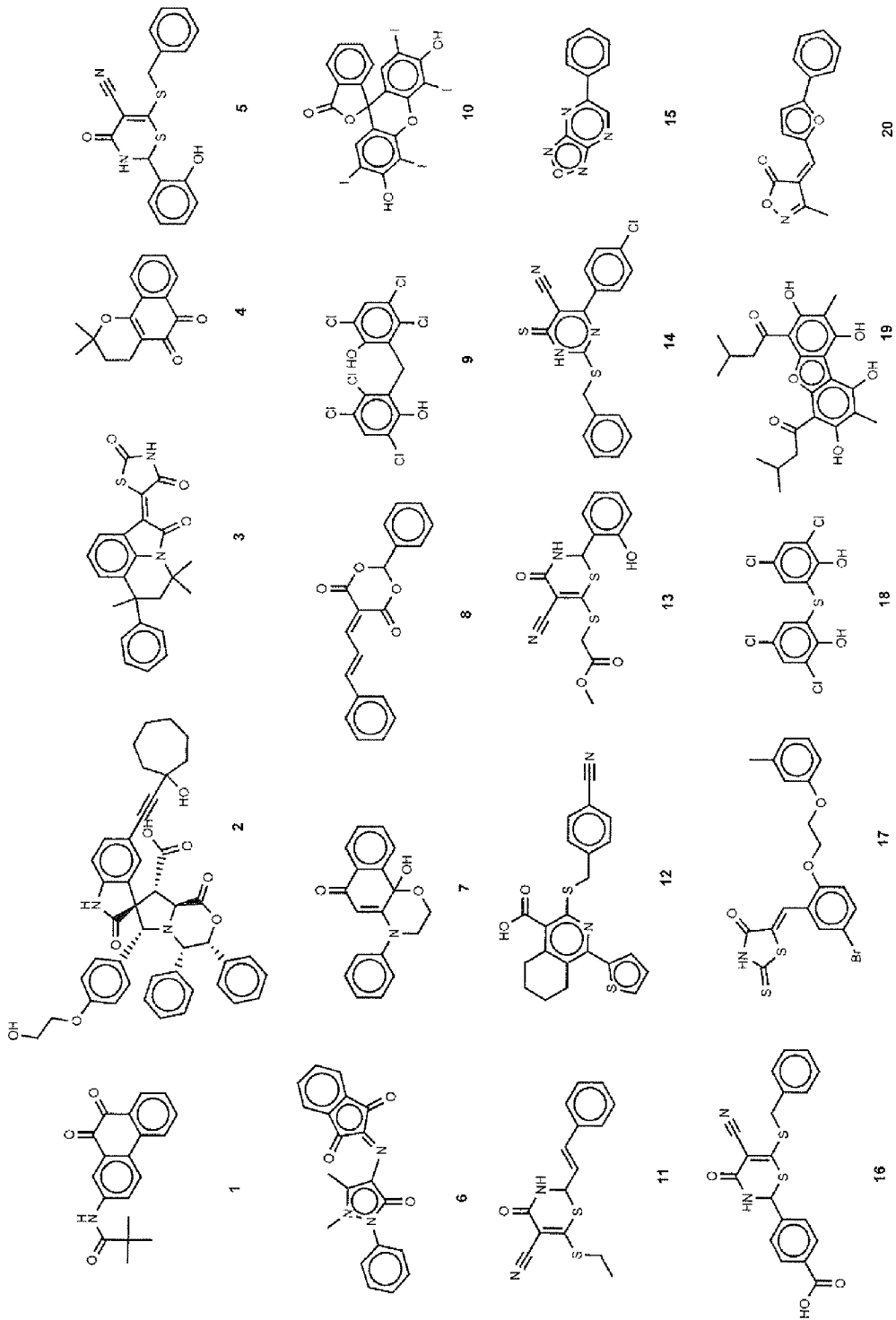
FIG. 6 is a schematic representation of the structures of some of the compounds that have been identified. Compounds are numbered by composite z-score in descending order. Frequent moieties present include, six membered dihydro thiazinone rings, five membered methylene-thiazolidinone rings, aromatic carboxylic rings, aromatic carboxylic acid, halo phenols.
Figure 6:
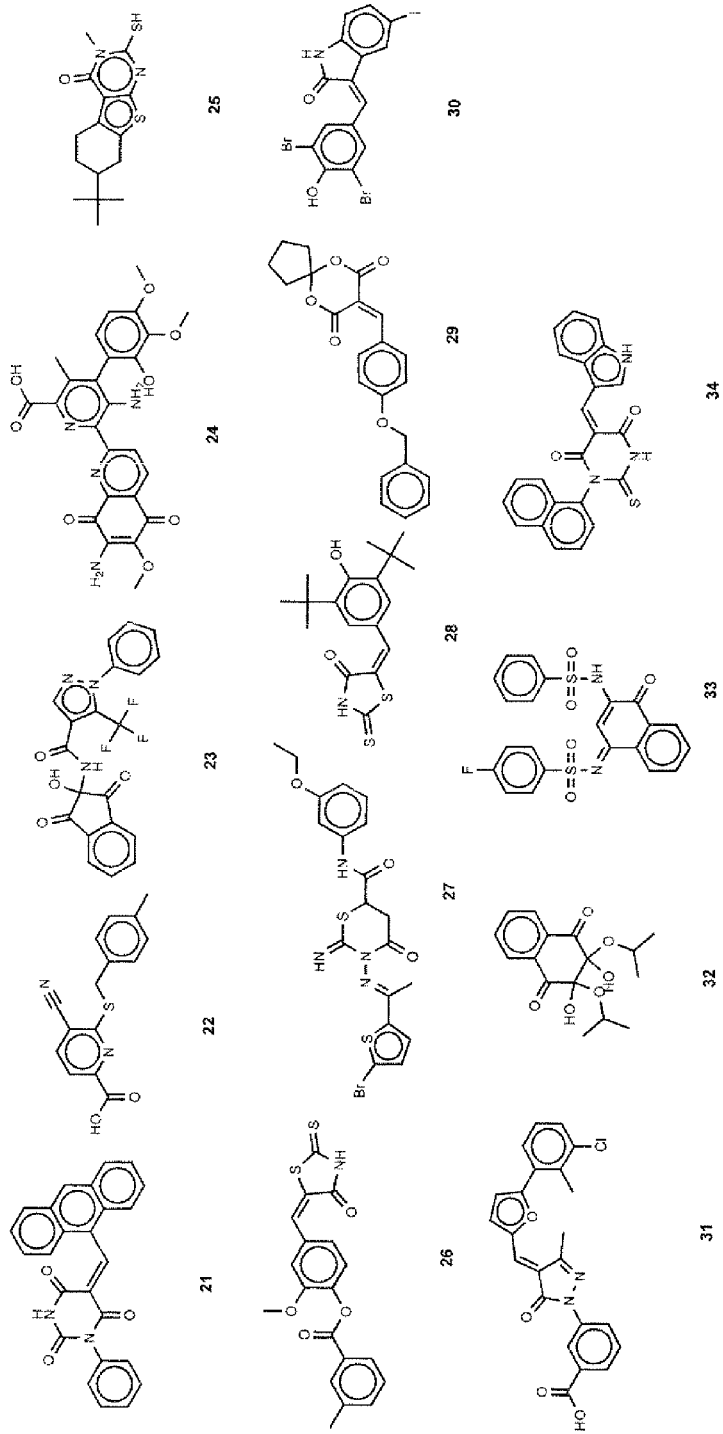

Confirmatory screen: FIG. 5 shows the correlation results between the luminescence values recorded for each of the selected 150 compounds in the primary screen and the confirmatory screen. A correlation coefficient of +0.48 was demonstrated. Following completion of the confirmatory screen, 34 compounds were selected for further characterization (FIG. 6). The other 116 compounds were excluded either because inhibitory properties on GALK activity were not confirmed in the confirmatory screen or because of known toxicity.

Preliminary characterization of the selected compounds: The molecular weights of the 34 identified structures were between approximately 200 and 800. They cover a relatively wide range of lipophilicity based on calculated log octanol-water partition coefficients in the −1 to 8 range (CLOGP from ChemDraw 10, CambridgeSoft). Most compounds had no Lipinski violations, and 10 compounds had 1 violation, with a maximum of 2 violations in 3 compounds.

Figure 7:
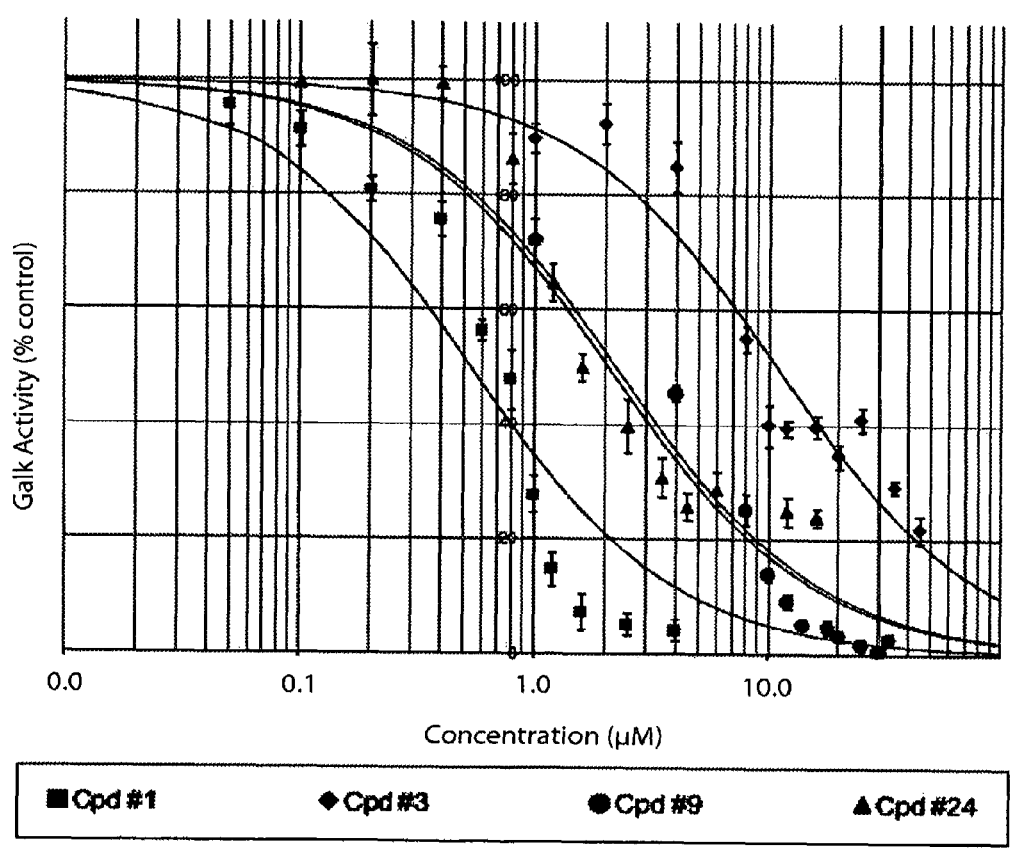
FIG. 7 is a graph showing the $IC_{50}$ for selected inhibitors. Dose response of the inhibition of galactokinase (GALK) activity in the standard pyruvate kinase/lactate dehydrogenase-coupled assay for compounds 1, 3, 9, and 24. Data are shown as a percentage of the corresponding controls (symbols representing mean±SD) and fitted with a standard log (inhibitor) versus response model (lines) to determine the median inhibitory $IC_{50}$ values.

The $IC_{50}$ of the compounds studied thus far using the established luminescence-based assay ranged from 200 nM to 33 µM. The $IC_{50}$ values of 4 selected representatives (compounds 1, 3, 9, and 24) have also been confirmed in the standard pyruvate kinase/lactate dehydrogenase-coupled assay (FIG. 7). In this assay, ATP consumed by the galactokinase reaction is recycled by the pyruvate kinase reaction, and the amount of galactose present in the reaction is in large excess; calculated reaction rates are close to initial velocity. Values obtained were somewhat lower than in the luminescence assay, which was in agreement with Wu and coworkers' observation that $IC_{50}$s determined at conditions other than zero substrate conversion would be higher than the true rate (*J Biomol Screen* 2003; 8:694-700).

All 34 compounds contained at least 2 rings, at least 1 of which was aromatic, and all had at least 2 hydrogen-bond acceptor sites. A pair of aromatic rings separated by 1, 2, or 3 bonds was the most common recurring motif. If one also considers rings flattened by at least 2 double bonds (and some resonance effects) such as those in structures 3, 5, 7, 8, 11, 13, 14, 16, 17, 21, 26, 27, 28, 31, 33, and 34, as a part of these pairs, then such a pair of close, flat rings is present in the majority of structures (31 of 34; separation of 1 bond: 1, 3, 5, 6, 8, 12, 13, 14, 15, 16, 19, 20, 21, 23, 24, 31, 34; 2 bonds: 3, 5, 6, 7, 9, 10, 17, 18, 19, 20, 21, 26, 28, 31, 34; 3 bonds: 1, 2, 5, 11, 12, 14, 16, 22, 23, 26, 27, 29, 30, 33). The remaining structures (4, 25, and 32) as well as some of the other ones (e.g., 1, 2, 6, 7, 23, 24, 30, 33) all contain an aromatic ring joined to a flat ring containing at least 1>C=O moiety. One of the most frequent motifs is a 6-membered dihydro-thiazinone ring, usually thio and cyano substituted (e.g., 5, 11, 13, 16, or 27; 14 having a similar ring), as well as a 5-membered methylene-thiazolidinone ring (e.g., 3, 17, 26, 28). A cyano substituent is present in 7 of the 34 structures. Most structures are neutral, nonionizable compounds: only 1 contains an ionizable aliphatic amine (2), but 6 contain an aromatic carboxylic acid (10-isomeric, 12, 16, 22, 24, and 31).

There are also quite a few halo-substituted phenols such as 9, 10, 18, and 30. Since there is considerable structural similarity among these 34 most promising compounds identified here, they can help in identifying an active binding site and serve as good leads for the development of an effective drug therapy for CG.

These compounds, identified in Tables 1 to 2, represent a starting point of a series of ongoing studies that are aimed to identify bioactive, potent, and selective GALK and other kinase inhibitors. One of the goals is that such inhibitors eventually will result in novel, medical treatment complementary to dietary therapy for patients with CG and other enzyme related diseases and disorders.

TABLE 1

| Compound Identifier | Compound Name (if known) | SMILES notation |
|---|---|---|
| HSCl1_000333 Calbiochem 540215 | Tyrosine Phosphatase CD45 inhibitor | CC(C)(C)C(=O)Nc1ccc-2c(c1)C(=O)C(=O)c3ccccc32 |
| PK04_097174 582836 Neumann | | OCCOc1ccc(cc1)[C@H]2N3[c@@H](C(=O)O)[C@]24C(=O)Nc5ccc(C#CC5(O)CCCCCC)cc54)C(=O)O[C@@H]([C@@H]3c7ccccc7)c8ccccc6 |
| TimTec1_006661 TimTec ST 4094742 | | CC1(C)CC(C)(C2ccccc2)c3cccc4/C(=O\5/SC(=O)NC5=O)/C(=O)N1c43 |
| HSCl1_000182 Calbiochem 428022 | b-Lapachone | CC1(C)CCC2=C(OI)c3ccccc C(=O)C2=O |
| ChemDiv3_007091 ChemDiv 7218-1573 | | Oc1ccccc1C2NC(=O)C(=C(SCc3ccccc3)S2)C#N |
| ChemDiv3_000368 ChemDiv 1184-1682 | | Cc1c(N=c2c(=O)c3ccccc3c2=O)c(=O)n(c4ccccc4)n1C |
| TimTec1_001881 TimTec ST026634 | | OC12OCCN(C2=CC(=O)c3ccccc31)c4ccccc4 |
| ChemDiv3_002016 ChemDiv 3553-1484 | | O=C1OC(OC(=O)C1=C/C=C/c2ccccc2)c3ccccc3 |
| SPBio_001210 | Hexachlorophene | Oc1c(Cl)cc(Cl)C1Cc2c(O)c(Cl)cc(Cl)C2Cl |
| SMP2_000049 Sigma E9259 | Erythrosin B | Oc1c(I)cc2c(Oc3c(I)c(O)c(I)cc3C42OC(=O)c5ccccc54)c11 |
| ChemDiv3_007133 ChemDiv 7218-1483 | | CCSC1=C(C#N)C(=O)NC(S1)/C=C/c2ccccc2 |
| TimTec1_001324 TimTec ST014236 | | OC(=O)c1c(SCc2ccc(C#N)cc1nc(c3cccs3)c4CCCCc14 |
| ChemDiv3_007089 ChemDiv 7218-1459 | | COC(=O)CSC1=1C(C(#N)C(=O)NC(S1)c2ccccc2O |
| Maybridge4_009132 JFD03061 | | Clc1ccc(cc1)c2nc(SCc3ccccc3)[nH]c(=S)c2C#N |
| TimTec1_000233 TimTec ST000572 | | c1ccc(cc1)c2cnc3nonc3n2 |
| ChemDiv3_014119 ChemDiv 7218-1576 | | OC(=O)c1ccc(cc1)C2NC(=O)C(=C(SCc3ccccc3)S2)C#N |
| ChemDiv3 001694 ChemDiv 3241-0272 | | Cc1ccc(OCCOc2ccc(Br)cc2/C=C/3\SC(=S)NC3=O)c1 |
| SPBio_000126 Spectrum2_000113 | Bithionol | Oc1c(Cl)cc(Cl)cc1Sc2cc(Cl)cc(Cl)c2O |
| SPBio_001697 Spectrum2_001629 | Rhodomyrtoxin | CC(C)CC(=O)c1c(O)c(C)c(O)c2c1oc3c(C(=O)CC(C)C)c(O)c(C)c(O)c32 |
| ChemDiv3_002334 ChemDiv 3696-0201 | | CC/1=NOC(=O)\C1=C\c2ccc(o2)c3ccccc3 |
| ChemDiv3_000903 ChemDiv 1887-0088 | | O=C1NC(=O)/C(=C\c2c3ccccc3cc4ccccc24)/C(=O)N1c5ccccc5 |
| TimTec1_001108 TimTec ST014268 | | Cc1ccc(CSc2nc(ccc2C#N)C(=O)O)cc1 |
| Maybridge4_001288 HTS08159 | | OC1(NC(=O)c2cnn(c2C(F)(F)F)c3ccccc3)C(=O)c4ccccc4C1=O |
| SMP2_000320 Sigma S1014 | Streptonigrin | COC1=C(N)C(=O)c2nc(ccc2C1=O)c3nc(C(=O)O)c(C)c(c3N)c4ccc(OC)c(OC)c4O |
| TimTec1_001055 TimTec ST012305 | | Cn1c(S)nc2sc3CC(CCc3c2c1=O)C(C)(C)C |
| ChemDiv3_001508 ChemDiv 3229-1543 | | COc1cc(/C=C\2/SC(=S)NC2=O)ccc1OC(=O)c3cccc(C)c3 |
| ChemDiv3_007160 ChemDiv 8012-2663 | | CCOc1cccc(NC(=O)C2CC(=O)N(/N=C(\C)/c3ccc(Br)s3)C(=N)S2)c1 |
| ChemDiv3_001677 ChemDiv 3062-0036 | | CC(C)(C)c1cc(/C=C/2\SC(=S)NC2=O)cc(c1O)C(C)(C)C |
| TimTec1_003525 TimTec ST048025 | | O=C1OC2(CCCC2)OC(=O)C1=Cc3ccc(OCc4ccccc4)cc3 |
| BiomolKI2_000062 BiomolEI-307 | | Oc1c(Br)cc(/C=C/2\C(=O)Nc3ccc(I)cc23)cc1Br |
| ChemDiv3_001693 ChemDiv 3175-0337 | | CC/1=NN(C(=O)\C1=C\c2ccc(c2)c3ccc(Cl)c3C)c4cccc(C4)C(=O)O |
| TimTec1_002320 TimTec ST032682 | | CC(C)OC1(O)C(=O)c2ccccc2C(=O)C1(O)OC(C)C |
| ChemDiv3_003365 ChemDiv 4456-1104 | | Fc1ccc(cc1)S(=O)(=O)/N=C/2\C=C(NS(=O)(=O)c3ccccc3)C(=O)c4ccccc24 |
| TimTec1_005567 TimTec ST 4029573 | | O=C/1NC(=S)N(C(=O)\C1=C\c2c[nH]c3ccccc23)c4ccc5ccccc45 |

| Compound Identifier | Compound Name (if known) | SMILES notation |
|---|---|---|
| HSCl1_000305 ChemDiv3_002459 | NF279 | OS(=O)(=O)c1cc(c2c(NC(=O)c3ccc(NC(=O)c4ccc(NC(=O)Nc5ccc(cc5)C(=O)Nc6ccc(cc6)C(=O)Nc7ccc(c8cc(cc(c78)S(=O)(=O)O)S(=O)(=O)O)S(=O)(=O)O)cc4)cc3)ccc(c2c1)S(O)(=O)O)S(=O)(=O)O COC(=O)/C(=C/C=C/c1ccccc1)/NC(=O)c2ccccc2 |
| HSCl1_000035 | ETYA | CCCCCC#CCC#CCC#CCCCC(=O)O |
| PK04_097255 | | OCCOc1ccc(cc1)[C@H]2N3[C@H]([C@H](C(=O)O)[C@@]24C(=O)Nc5ccc(C#CC6(O)CCCCCC6)cc54)C(=O)O[C@H]([C@H]3c7cccc7)c8ccccc8 |
| PK04_098179 | | OCCOc1ccccc1[C@H]2N3[C@@H]([C@@H](C(=O)O)[C@]24C(=O)Nc5ccc(C#CC6(O)CCCCCC6)cc54)C(=O)O[C@@H]([C@@H]3c7ccccc7)c8ccccc8 |
| HSCl1_000331 | Fascaplysin | O=C1c2ccccc2-[n+]3ccc4c5ccccc5[nH]c4c13 |
| HSCl1_000187 | MEK Inhibitor II | ClC1=C(N2C(=O)CCC2=O)C(=O)c3ccccc3C1=O |
| Maybridge4_003162 | | CC(C)(C)C(=O)Nc1ccc(c1)c2cc(no2)c3c(Cl)cccc3Cl |
| ACon1_002474 | NP-006428 | CCCCCc1cc(OC)c2CC(O)C(C)(C)Oc2c1C(=O)O |
| Maybridge4_002460 | | OC(=O)C1Cc2ccccc2C1 |
| HSCl1_000002 | Raf1 Kinase Inhibitor I | Oc1c(Br)cc(/C=C/2\C(=O)Nc3ccc(I)cc23)cc1Br |
| ACon1_001911 | NP-005324 | OC1(OCC2C(OCC21O)c3ccc4OCOc4c3)c5ccc6OCOc6c5 |
| SMP2_000091 | aurintricarboxylic acid | NOC(=O)C1=CC(=C(c2ccc(O)c(c2)C(=O)ON)c3ccc(O)c(c3)C(=O)ON)C=CC1=O |
| ChemDiv3_006723 | | CCn1nc(N)c2c(O)nc(C)cc12 |
| ChemDiv3_000237 | | O=C1C(C(C2C(=O)c3ccccc3C2=O)c4ccccc4)C(=O)c5ccccc15 |
| PK04_097046 | | NC(=O)NCC#Cc1ccc2NC(=O)[C@@]3([C@H][C@H]4N([C@H]3c5ccccc5OCCO)[C@@H]([C@@H](OC4=O)c6ccccc6)c7ccccc7)C(=O)O)c2c1 |
| PK04_097081 | | COc1ccc(C#Cc2ccc3NC(=O)[C@]4([C@@H][C@@H]5N([C@@H]4c6ccc(OCCO)cc6)[C@H]([C@H](OC5=O)c7ccccc7)c8ccccc8)C(=O)O)c3c2)cc1 |

-continued

| Compound Identifier | Compound Name (if known) | SMILES notation |
|---|---|---|
| HSCl1_000004 | BH3I -2? | Oc1c(1)cc(Cl)cc1C(=O)Nc2cc(ccc2Cl)S(=O)(=O)c3ccc(Cl)cc3 |
| ChemDiv3_015769 | | COC(=O)Cn1cc2CCc3oc(C(=O)N4CCCC4)c(C)c3-c2n1 |
| PK04_097057 | | OCCOc1ccccc1[C@@H]2N3[C@H]([C@H](C(=O)O)[C@@]24C(=O)Nc5ccccc54)C(=O)O[C@H]([C@H]3c6ccccc6)c7ccccc7 |
| TimTec1_000037 | | OC(=O)c1cccc(CN2CCN(CC2)c3ccccc3)c1 |
| SPBio_000035 | epigallocatechin-3-monogallate | Oc1cc(O)c2C[C@@H](OC(=O)c3cc(O)c(O)c(O)c3)[C@H](Oc2c1)c4cc(O)c(O)c(O)c4 |
| PK04_098125 | | OCCOc1ccc(cc1)[C@@H]2N3[C@@H]([C@@H](C(=O)O)[C@]24C(=O)Nc5ccc(C#CC6=CCCCC6)cc54)C(=O)O[C@@H]([C@@H]3c7ccccc7)c8ccccc8 |
| SPBio_000341 | 1,4-naphthoquinone | O=C1C=CC(=O)c2ccccc12 |
| PK04_097018 | | COc1ccc(C#Cc2ccc3NC(=O)[C@@]4([C@H]([C@H]5N([C@H]4c6ccc(O)cc6)[C@@H]([C@@H](OC5=O)c7ccccc7)c8ccccc8)C(=O)O)c3c2)cc1 |
| HSCl1_000315 | Benzopurpurin (B) | Cc1cc(ccc1N=Nc2cc(c3ccccc3c2N)S(=O)(=O)O)c4ccc(N=Nc5cc(c6ccccc6c5N)S(=O)(=O)O)c(C)c4 |
| PK04_097253 | | COC(=O)C(CC#Cc1ccc2NC(=O)[C@@]3([C@H]([C@H]4N([C@H]3c5ccccc5OCCO)[C@@H]([C@@H](OC4=O)c6ccccc6)c7ccccc7)C(=O)O)c2c1)C(=O)OC |
| ChemDiv3_014394 | | O=C/1Nc2ccccc2\C1=C\c3ccccc3 |
| SPBio_000394 | epigallocatechin 3,5-d igallate | Oc1cc(OC(=O)c2cc(O)c(O)c(O)c2)c3C[C@@H](OC(=O)c4cc(O)c(O)c(O)c4)[C@H](Oc3c1)c5cc(O)c(O)c(O)c5 |
| SPBio_000649 | theaflavin digallate | Oc1cc(O)c2C[C@@H](OC(=O)c3cc(O)c(O)c(O)c3)[C@H](Oc2c1)c4cc(O)c(O)c5c(=O)c(O)cc(cc45)[C@H]6Oc7cc(O)cc(c7[C@H]6OC(=O)c8cc(O)c(O)c(O)c8 |
| ChemDiv3_001455 | | CCCCc1oc2ccccc2c1C(=O)c3ccc(O)cc3 |
| ChemDiv3_003258 | | OC(=O)c1cccc(c1)S(=O)(=O)/N=C\2/C=C(NS(=O)(=O)c3ccccc3)C(=O)c4ccccc24 |
| ChemDiv3_002419 | | Oc1occ2ccccc2c1/C=N/S(=O)(=O)c3ccccc3 |
| PK04_097003 | | COc1ccc(C#Cc2ccc3NC(=O)[C@@]4([C@H]([C@H]5N([C@H]4c6ccc(OCCO)cc6)[C@@H]([C@@H](OC5=O)c7ccccc7)c8ccccc8)C(=O)O)c3c2)cc1 |
| ChemDiv3_000127 | | COc1ccccc(c1)C2(CCCC2)c3ccc(O)cc3 |
| ACon1_001054 | NP-003608 | Oc1cc(O)c2C[C@@H](OC(=O)c3cc(O)c(O)c(O)c3)[C@H](Oc2c1)c4cc(O)c(O)c(O)c4 |
| ChemDiv3_000428 | | Cn1c(c(/C=C\2/C(=O)Oc3ccccc3C2=O)c4ccccc14)c5ccccc5 |
| Maybridge4_000719 | | Clc1ccc(NC(=O)C(C#N)C(=O)c2cccs2)cc1 |
| PK04_097149 | | OCCOc1ccc(cc1)[C@@H]2N3[C@H]([C@H](C(=O)O)[C@@]24C(=O)Nc5ccc(G#CC6=CCCCC6)cc54)C(=O)O[C@H]([C@H]3c7ccccc7)c8ccccc8 |
| P K04_097012 | | COc1ccc(C#Cc2ccc3NC(=O)[CO]4([C@@H]([C@@H]5N([C@@H]4c6ccc(O)cc6)[COH]([C@H](OC5=O)c7ccccc7)c8ccccc8)C(=O)O)c3c2)cc1 |
| PK04_097295 | | COC(=O)C(CC#Cc1ccc2NC(=O)[C@@]3([C@H]([C@H]4N([C@H]3c5ccc(OCCO)cc5)[C@@H]([C@@H](OC4=O)c6ccccc6)c7ccccc7)C(=O)O)c2c1)C(=O)OC |
| Maybridge4_000547 | | OCC(O)Cn1c2ccc(Br)cc2c3cc(Br)ccc13 |
| Maybridge4_000383 | | CSC1=C(C#N)C(=O)NC(S1)c2ccc(Cl)cc2 |
| HSCl1_000319 | Calmidazolium Chloride | Clc1ccc(cc1)C(c2ccc(Cl)cc2)[n+]3ccn(CC(OCc4ccc(Cl)cc4C1)c5ccc(Cl)cc5Cl)c3 |
| ChemDiv3_012072 | | CCn1cc2CCc3oc(C(=O)Nc4ccc(Cl)cc4)c(C)c3-c2n1 |
| SPBio_000927 | cobalamine | CC1CNC(=O)CCC2(C)C(CC(=O)N)C3N4C2=C(C)C5=N6C(=CC7=N8C(=C(C)C9=N(C3(C)C(C)(CC(=O)N)C9CCC(=O)N)[Co+]486(C[C@H]%10OC([C@H](O)[C@@H]%10O)n%11cnc%12c(N)ncnc%11%12)N%13=CN(C%14O[C@H](CO)[C@@H](OP(=O)(O)O1)[C@H]%14O)c%15cc(C)c(C)cc%13%15)C(C)(CC(=O)N)C7CCC(=O)N)C(C)(C)C5CCC(=O)C |
| SPBio_000031 | 2',2'-bisepigallocatechin digallate | Oc1cc(O)c2C[C@@H](OC(=O)c3cc(O)c(O)c(O)c3)[C@H](Oc2c1)c4cc(O)c(O)c(O)c4c5c(O)c(O)c(O)cc5[C@H]6Oc7cc(O)cc(O)c7C[C@H]6OC(=O)c8cc(O)c(O)c(O)c8 |
| HSCl1_000222 | Pseudohypericin | Cc1cc(O)c2c(=O)c3c(O)cc(O)cc4c5c(O)cc(O)c6c(=O)c7c(O)cc(CO)c8c1c2c(c34)c(c65)c78 |
| PK04_098045 | | OC(=O)[C@@H]1[C@H]2N([COH](c3ccc(O)cc3)[C@@]14C(=O)Nc5ccc(C#CC6(O)CCCCCC6)cc54)[COH]([C@H](OC2=O)c7ccccc7)c8ccccc8 |
| ChemDiv3_011472 | | Cc1cc2ncn(CCC3CCCCC3)c2cc1C |
| Maybridge4_000280 | | CCCN(CCC)S(=O)(=O)c1ccc(cc1)C(=O)N2CC3CCCC(CC3)C2 |
| HSCl1_000113 | BH3I-1 | CC(C)C(N1C(=O)/C(=C/c2ccc(Br)cc2)/SC1=S)C(=O)O |
| TimTec1_002292 | | Oc1ccc(Cl)cc1Sc2cc(Cl)ccc2O |
| SPBio_000029 | epicatechin monogallate | Oc1cc(O)c2C[C@@H](OC(=O)c3cc(O)c(O)c(O)c3)[C@H](Oc2c1)C4ccc(O)c(O)c4 |
| Maybridge4_000025 | | CN(/N=C/c1cc(Cl)cc(Cl)c1O)C(=S)NC(C)(C)C |
| SPBio_000260 | celastrol | CC1=C(O)C(=O)C=C2C1=CC=C3[C@@]2(C)CC[C@@]4(C)[C@@H]5C[C@@](C)(CC[C@]5(C)CC[C@]34C)C(=O)O |
| TimTec1_006170 | | Cc1nc(Cl)c2sc(=S)n(c3ccccc3)c2n1 |
| HSCl1_000274 | Protein Tyrosine Phosphatase Inhibitor IV | CC(C)(c1ccc(NS(=O)(=O)C(F)(F)F)cc1)c2ccc(cc2)C(C)(C)c3cccc(NS(=O)(=O)C(F)(F)F)c3 |

-continued

| Compound Identifier | Compound Name (if known) | SMILES notation |
|---|---|---|
| PK04_098207 | | COC(=O)C(CC#Cc1ccc2NC(=O)[C@]3([C@@H]([C@@H]4N([C@@H]3c5ccccc5OCCO)[C@H]([C@H](OC4=O)c6ccccc6)c7ccccc7)C(=O)O)c2c1)C(=O)OC |
| SPBio_001687 | gossypol | CC(C)c1c(O)c(O)c(C=O)c2c(O)c(c(CCc12)c3c(C)cc4c(C(C)C)c(O)c(O)c(C=O)c4c3O |
| ChemDiv3_000631 | | COc1cccc(/N=C\c2c[nH]c3ccccc23)c1 |
| SPBio_000023 | theaflavin monogallates | O[C@@H]1Cc2c(O)cc(O)cc2O[C@@H]1c3cc(O)c(O)c4c(=O)c(O)cc(cc34)[C@H]5Oc6cc(O)cc(O)c6C[C@H]5OC(=O)c7cc(O)c(O)c(O)c7 |
| PK04_097102 | | OCCOc1ccccc1[C@@H]2N3[C@H]([C@H](C(=O)O)[C@@]24C(=O)Nc5ccc(C#CC6=CCCCC6)cc54)C(=O)O[C@H]([C@H]3c7ccccc7)c8ccccc8 |
| Maybridge4_001879 | | O=C1/C(=C/c2ccc(cc2)c3nnn[nH]3)/C(Oc4ccccc14)c5ccccc5 |
| SPBio_002863 | Propidium iodide | CC[N+](C)(CC)CCC[n+]1c(c2ccccc2)c3cc(N)ccc3c4ccc(N)cc14 |
| ChemDiv3_012460 | | COc1ccc(NC(=O)c/2cc3ccc(O)cc3o\c2=N/c4ccc(cc4)C(=O)O)cc1 |
| ChemDiv3_014894 | | COc1ccc(CCn2c(C)c3c(=O)n([nH]c3cc2=O)c4nc5ccccc5s4)cc1 |
| Maybridge4_002594 | | NNC(=S)c1cc(Cl)cc(Cl)c1 |
| HSCl1_000296 | NF449 | OS(=O)(=O)c1ccc(NC(=O)c2cc(NC(=O)Nc3cc(cc(c3)C(=O)Nc4ccc(cc4S(=O)(=O)O)S(=O)(=O)O)C(=O)Nc5ccc(cc5S(=O)(=O)O)S(=O)O)cc(c2)C(=O)Nc6ccc(cc6S(=O)(=O)O)S(=O)(=O)O)c(c1)S(=O)(=O)O |
| PK04_098211 | | OC(=O)[C@@H]1[C@@H]2N([C@H](c3ccc(O)cc3)[C@@]14C(=O)Nc5ccc(C#CC6=CCCCC6)cc54)[C@H]([C@H](OC2=O)c7ccccc7)c8ccccc8 |
| ChemDiv3_014798 | | Cc1cc(OCC(=O)NC(Cc2c[nH]c3ccccc23)C(=O)O)cc(C)c1Cl |
| SPBio_001777 | tetrachloroisophthalonitrile | Clc1c(Cl)c(C#N)c(Cl)c(C#N)c1Cl |
| HSCl1_000387 | Reversine | ClCCC(CC1)Nc2nc(Nc3ccc(cc3)N4CCOCC4)nc5[nH]cnc25 |
| HSCl1_000078 | Licochalcone-A | COc1cc(O)c(cc1/C=C/C(=O)c2ccc(O)cc2)C(C)(C)C=C |
| PK04_097298 | | COC(=O)C(CC#Cc1ccc2NC(=O)[C@]3([C@@H]([C@@H]4N([C@@H]3c5ccc(OCCO)cc5)[C@H]([C@H](OC4=O)c6ccccc6)c7ccccc7)C(=O)O)c2c1)C(=O)OC |
| PK04_098190 | | OCCOc1ccccc1[C@H]2N3[C@@H]([C@@H](C(=O)O)[C@]24C(=O)Nc5ccc(C#CC6=CCCCC6)cc54)C(=O)O[C@@H]([C@@H]3c7ccccc7)c8ccccc8 |
| ChemDiv3_000384 | | O=C1NC(=O)C(=Cc2ccc(o2)c3ccccc3)C(=O)N1 |
| P K04_097016 | | NC(=O)NCC#Cc1ccc2NC(=O)[C@@]3([C@H]([C@@H]4N([C@H]3c5ccc(OCCO)cc5)[C@@H]([C@@H](OC4=O)c6ccccc6)c7ccccc7)C(=O)O)c2c1 |
| ACon1_001710 | NP-000870 | OC(=O)[C@]1(C[C@@H](OC(=O)/C=C/c2ccc(O)c(O)c2)[C@@H](OC(=O)/C=C/c3ccc(O)c(O)c3AC@@H](C1)OC(=O)/C=C/c4ccc(O)c(O)c4)OC(=O)/C=C/c5ccc(O)c(O)c5 |
| PK04_097049 | | NC(=O)NCC#Cc1ccc2NC(=O)[C@]3([C@@H]([C@@H]4N([C@@H]3c5ccc(OCCO)cc5)[C@H]([C@H](OC4=O)c6ccccc6)c7ccccc7)C(=O)O)c2c1 |
| TimTec1_001159 | | OC(=O)c1ccc(cc1)c2cc(c3cccs3)c(C#N)c(SCc4cccs4)n2 |
| TimTec1_001097 | | CC(=O)Nc1nonc1/N=C\c2ccc(F)cc2 |
| SPBio_000420 | cetrimonium bromide | CCCCCCCCCCCCCCCC[N+](C)(C)C |
| ICCB6_000340 | II_HO5 | OCCOc1ccc(cc1)[C@@H]2N3[C@@H]([C@@H](C(=O)O)[C@]24C(=O)Nc5ccc(C#CC6(O)CCCCCC6)cc54)C(=O)O[C@@H]([C@@H]3c7ccccc7)c8ccccc8 |
| HSCl1_000133 | I—OMe—AG 538 | COc1cc(/C=C(\C#N)/C(=O)c2ccc(O)c(O)c2)cc(I)c1O |
| HSCl1_000357 | K-252c | O=C1NCc2c1c3c4ccccc4[nH]c3c5[nH]c6ccccc6c25 |
| TimTec1_001160 | | CC1=C(C(C(=C(S)S1)C#N)c2ccc[nH]2)C(=O)OCc3ccccc3 |
| Maybridge4_003860 | | OC(=O)CC1(CC(=O)Nc2cc3ccccc3cn2)CCCCC1 |
| HSCl1_000306 | AGL 2263 | Oc1ccc(cc1O)C(=O)/C=C/c2ccc3oc(=O)[nH]c3c2)/C#N |
| TimTec1_005643 | | CNC(=S)N(C)/N=C\1/C(=O)N(Cc2c(Cl)cccc2Cl)c3ccccc13 |
| TimTec1_000797 | | NC(CSCc1oc(cc1C(=O)O)c2ccccc2)C(=O)O |
| ACon1_002102 | NP-005115 | O[C@H]1[C@H]2[C@H](CC(=O)O)C(=O)O[C@@H]3C(COC(=O)c4cc(O)c(O)c(O)c4)O[C@@H](OC(=O)c5cc(O)c(O)c(O)c5)C(=O)c6cc(O)c(O)c(OC1=O)c26)[C@@H]3OC(=O)c7cc(O)c(O)c(O)c7 |
| ChemDiv3_006929 | | CC1(C)CC(=O)C2=C(C1)NC(=NC2c3ccccc3)Nc4nc5ccccc5o4 |
| PK04_098021 | | OCCOc1ccccc1[C@@H]2N3[COH]([C@H](C(=O)O)[C@@]24C(=O)Nc5ccc(C#CC6(O)CCCCCC6)cc54)C(=O)O[C@H]([C@H]3c7ccccc7)c8ccccc8 |
| ChemDiv3_007117 | | CC(C)(C)c1cc(cc(c1O)C(C)(C)C)C(N2CCOCC2)c3ccc(O)cc3 |
| SPBio_000585 | tannic acid | Oc1cc(cc(c1O)C(=O)Oc2cc(cc(O)c2O)C(=O)OC[C@H]3O[C@H](OC(=O)c4cc(O)c(O)c(OC(=O)c5cc(O)c(O)c(O)c5)c4)[C@H](OC(=O)c6cc(O)c(O)c(OC(=O)c7cc(O)c(O)c(O)c7)c6)[C@@H](OC(=O)c8cc(O)c(O)c(OC(=O)c9cc(O)c(O)c(O)c9)c8)[C@@H]3OC(=O)c%1ccc(O)c(O)c(OC(=O)c%11cc(O)c(O)c(O)c%11)c%10 |
| Maybridge4_004121 | | NC(=S)c1cc(c(s1)C(F)(F)F)c2ccccc2 |
| PK04_097115 | | OCCOc1ccc(cc1)[C@@H]2N3[C@H]([C@H](C(=O)Nc4nc5ccccc5s4)[C@@]26C(=O)Nc7ccc(C#CC8(O)CCCCCC8)cc76)C(=O)O[C@H]([C@H]3c9ccccc9)c%10ccccc%10 |
| TimTec1_006683 | | COc1cccc(c1)N2C(=O)CN=C2Nc3nc(C)cc(C)n3 |

-continued

| Compound Identifier | Compound Name (if known) | SMILES notation |
|---|---|---|
| ChemDiv3_000908 | | OC(=O)c1ccccc1n2c(=O)c3cc4c(=O)n(c5ccccc5C(=O)O)c(=O)c4cc3c2=O |
| HSCl1_000235 | ACA | CCCCCCc1ccc(/C=C/C(=O)Nc2ccccc2C(=O)O)cc1 |
| HSCl1_000115 | NSC 119889 | OC(=O)c1c(Br)c(Br)c(Br)c1c2c3ccc(O)cc3oc4cc(=O)ccc24 |
| HSCl1_000198 | PDGF Receptor Tyrosine Kinase Inhibitor I | Oc1ccc2[nH]c(cc2c1)C(=O)c3cc4ccccc4[nH]3 |
| ChemDiv3_014504 | | OC(=O)C1=Cc2sc3CCCCc3c2CS1 |
| PK04_098163 | | COc1ccc(C#Cc2ccc3NC(=O)[C@@]4[C@H]([C@H]5N([C@H]4c6ccccc6OCCO)[C@@H]([C@@H](OC5=O)c7ccccc7)c8ccccc8)C(=O)O)c3c2)cc1 |
| PK04_098082 | | OCCOc1ccc(cc1)[C@H]2N3[C@@H]([C@@H](C(=O)O)(C@]24C(=O)Nc5ccc(C#CCCO)cc54)C(=O)O[C@@H]([C@@H]3c6ccccc6)c7ccccc7 |
| BiomolKI2_000009 | | CC(C)(C)c1cc(C=C(C#N)C#N)cc(c1O)C(C)(C)C |
| PK04_098199 | | COCCOC(=O)N1C(=O)[C@]2([C@@H]([C@@H]3N([C@@H]2c4ccccc4OCCO)[C@H]([C@H](OC3=O)c5ccccc5)c6ccccc6)C(=O)Nc7nc8ccccc8s7)c9cc(C#CC%10(O)CCCCCC%10)ccc19 |
| ChemDiv3_011481 | | CC(C)c1ccc(NC(=O)c2ccc3snnc3c2)cc1 |
| PK04_097282 | | OCCOc1ccc(cc1)[C@@H]2N3[C@H]([C@H](C(=O)O)[C@@]24C(=O)Nc5ccc(C#CCCO)cc54)C(=O)O[COH]([C@H]3c6ccccc6)c7ccccc7 |
| HSCl1_000048 | 1-Stearoyl-2-arachidonoyl-sn-glycerol | CCCCCCCCCCCCCCCCCC(=O)OCC(CO)OC(=O)CCC/C=C/C/C=C/C\C=C\C\C=C\CCCCC |
| PK04_097194 | | COCCOC(=O)N1C(=O)[CO]2[C@@H]([C@@H]3N([C@@H]2c4ccc(O)cc4)[C@H]*([C@H](OC3=O)c5ccccc5)c6ccccc6)C(=O)N)c7cc(C#CCC(C(=O)OC)C(=O)OC)ccc17 |
| HSCl1_000332 | WR 216174 | Fc1ccc(cc1)C(=O)/C=C/2\C(=O)Nc3ccc(Br)cc23 |
| ChemDiv3_005246 | | FC(F)(F)c1cccc(c1)S(=O)(=O)NC2(CC3CC4CC(C3)C2)C4 |
| PK04_097319 | | OC(=O)[C@H]1 [C@@H]2N([C@@H](c3ccc(O)cc3)[C@]14C(=O)Nc5ccc(G#CC6=CCCCC6)cc54)[C@@H]([C@@H](OC2=O)c7ccccc7)c8ccccc8 |
| TimTec1_004971 | | Cc1ccc(SC(CC(=O)c2ccc(cc2)C(C)(C)C)C(=O)O)cc1 |
| HSCl1_000249 | Cdk1 Inhibitor | Clc1[nH]c2ccccc2c1/C=C\3/C(=O)Nc4ccccc34 |
| ChemDiv3_004096 | | OC(=O)c1ccc(cc1)c2ccc(/C=C\3/SC(=NC3=O)Nc4cccc(c4)C(=O)O)o2 |
| ChemDiv3_008579 | | CCc1ccc(NC(=O)CSc2nc3CC(C)Sc3c(=O)n2CC)cc1 |
| HSC I1_000346 | U-73343 | COc1ccc2C3CC[C@]4(C)[C@H](CCC4C3CCc2c1)NCCCCCCN5C(=O)CCC5=O |
| PK04_097275 | | Oc1ccc(cc1)[C@H]2N3[C@@H]([C@@H](C(=O)N4CCN(CC4)c5ncccn5)[C@]26C(=O)Nc7ccc(C#CC8(O)CCCCCC8)cc76)C(=O)O[C@@H]([C@@H]3c9ccccc9)c%10ccccc%10 |
| PK04_097009 | | OCCCOc1ccccc1[C@@H]2N3[C@H]([C@@H](C(=O)O)[C@@]24C(=O)Nc5ccc(C#CCCO)cc54)C(=O)O[C@H]([C@H]3c6ccccc6)c7ccccc7 |
| ChemDi v3_004268 | | OC(=O)c1ccc(cc1)N2N=C(/C(=C/c3ccc(OC(=O)c4cccs4)cc3)/C2=O)C(F)(F)F |
| Maybridge4_000651 | | CCCN(CCC)S(=O)(=O)c1ccc(cc1)C(=O)Nc2ccc(SC)c2 |
| HSCl1_000020 | AG 835 | C[C@H](NC(=O)/C=C/c1ccc(c(O)cc1)/C#N)c2ccccc2 |
| PK04_096001 | | COc1ccc(CCNC(=O)[C@]2(Cc3ccccc31)[C@@H](N(C4CCCCC4)C(=O)c5ccccc52)c6ccc(CO)cc6)cc1 |
| PK04_097317 | | NC(=O)NCC#Cc1ccc2NC(=O)C(@]3([C@@H]([C@@H]4N([C@@H]3c5ccccc5OCCO)[C@@H]([C@H](OC4=O)c6ccccc6)c7ccccc7)C(=O)O)c2c1 |
| ChemDiv3_014350 | | O=C/1Nc2ccccc2\C1=C\C3CCC=CC3 |
| ChemDiv3_000637 | | OC(=O)c1cc(ccc1O)C2(CC3CC4CC(C3)C2)C4 |
| HSCl1_000294 | NF023 | OS(=O)(=O)c1cc(c2c(NC(=O)c3cccc(NC(=O)Nc4cccc(c4)C(=O)Nc5ccc(c6cc(cc(c56)S(=O)(=O)O)S(=O)(=O)O)S(=O)(=O)O)c3ccc(c2c1)S(=O)(=O)O)S(=O)(=O)O |
| ChemDiv3_007090 | | Cc1ccc(cc1)n2sc3ccccc3c2=O |
| Maybridge4_001879 | | O=C1/C(=C/c2ccc(cc2)c3nnn[nH]3)/C(Oc4ccccc14)c5ccccc5 |
| HSCl1_000185 | AG 17 | CC(C)(C)c1cc(C=C(C#N)C#N)cc(c1O)C(C)(C)C |
| ACon1_001657 | NP-003586 | OC(=O)C(OC(=O)/C=C/c1ccc(O)c(O)c1)C(OC(=O)/C=C/c2ccc(O)c2)C(OC(=O)/C=C/c3ccc(O)c(O)c3)C(OC(=O)/C=C/c4ccc(O)c(O)c4)C(=O)O |
| BiomolK12_000004 | | O=c1cc(oc(c1)c2ccccc3Sc4ccccc4Sc23)N5CCOCC5 |
| SPBio_000589 | tetrac | OC(=O)Cc1cc(1)c(Oc2cc(1)c(O)c(1)c2)c(1)c1 |
| PK04_098003 | | OCCOc1ccccc1[C@@H]2N3[C@@H]([C@@H](C(=O)O)[C@@]24C(=O)Nc5ccccc54)C(=O)O[C@@H]([C@@H]3c6ccccc6)c7ccccc7 |
| PK04_130094 | | CO[C@H](CCO)[C@H](OC(=O)Nc1ccc(OC)cc1)c2ccc(OC)c(O)c2 |
| ChemDiv3_016344 | | CC1CN(C(=O)C)c2ccc(cc2O1)S(=O)(=O)N(C)Cc3ccccc3 |
| ICCB6_000298 | II_G06 | OCCOc1ccc(cc1)[C@H]2N3[C@@H]([C@@H](C(=O)O)(C@@]24C(=O)Nc5ccc(C#CC6CCCCC6)cc54)C(=O)O[C@@H]([C@@H]3c7ccccc7)c8ccccc8 |

-continued

| Compound Identifier | Compound Name (if known) | SMILES notation |
|---|---|---|
| ChemDiv3_004352 | | COc1cc(/C=C/2\C(=NOC2=O)C)cc(Cl)c1OCc3ccc(C)cc3 |
| SMP2_000306 | kenpaullone | Brc1ccc2[nH]c-3c(CC(=O)Nc4ccccc34)c2c1 |
| PK04_097293 | | COc1ccc(C#Cc2ccc3NC(=O)[C@@]9 4([C@H]([C@H]5N([C@H]4c6ccc(OCCO)cc6)[C@@H]([C@@H](OC5=O)c7ccccc7)c8ccccc8)C(=O)Nc9nc%10ccccc%10s9)c3c2)cc1 |
| ChemDiv3_001801 | | O=c1n(Cc2ccccc2)c(=S)[nH]c3sc4CCCCCc4c13 |
| ChemDiv3_012486 | | O=C(Cc1ccccc1)Nn2c(SCC(=O)c3ccccc3)nc4ccccc4c2=O |
| HSCl1_000032 | AG 1024 | CC(C)(C)c1cc(C=C(G#N)C#N)cc(Br)c1O |
| TimTec1_002520 | | Cc1cc(C)cc(/N=C/c2ccc(C#N)cc2)c1 |
| Maybridge4_001966 | | OC(=O)c1ccccc1NC(=O)OCC2c3ccccc3-c4ccccc24 |
| ChemDiv3_014059 | | O=C(CCC(=O)c1ccccc1)Nc2ccccc2 |
| PK04_130132 | | OCCC[C@H](O)c1ccc(O)c(F)c1 |
| ICCB6_000268 | I_G02 | OCc1ccc(o1)[C@H]2N3[C@H]([C@H](C#N)[C@@]24C(=O)Nc5ccc(1)cc54)C(=O)O[COH]([C@H]3c6ccccc6)c7ccccc7 |
| ACon1_000576 | NP-011428 | COc1ccc(cc1)c2oc3cc(O[C@@H]4O[C@@H]([C@@H](O)[C@@H](O)(C@H]4O)cc(O)c3c(=O)c2O[C@@H]5O[C@H](CO)[C@@H](O)[C@H](O)(C@H]5O |
| ChemDiv3_014037 | | Cc1ccc(C)c(c1)N2CCN(CC2)C(=O)c3ccc(/C=C/4 \Oc5ccccc5NC4=O)cc3 |
| ChemDiv3_016150 | | Cc1ccc2cnn(CCCC(=O)Nc3ccccc3)c2c1 |
| Biomol KI2_000036 | | CC(C)(C)c1cc(/C=C( \C#N)/C(=S)N)cc(c1O)C(C)(C)C |
| ChemDiv3_007069 | | CC1(C)C2(C)CCC1(C(=O)O)c3nc4ccc5riccccc5c4nc32 |
| HSCl1_000103 | AG 957, Adamantyl Ester | Oc1ccc(O)c(CNc2ccc(cc2)C(=O)OC3(CC4CC5CC(C4)C3)C5)c1 |
| HSCl1_000036 | GSK-3b Inhibitor III | O=c1sn(Cc2ccccc2)c(=S)n1Cc3ccccc3 |
| HSCl1_000183 | Cucurbitacin I | CC(C)(O)/C=C/C(=O)[C@](C)(O)C1[C@H](O)C[C@@]2([C)[C@@H]3CC=C4C(=C(O)C=C(O)C4(C)C)[C@]3(C)C(=O)C[C@@]12C |
| ChemDiv3_002888 | | Cc1ccc(/C=C\2/SC(=O)NC2=S)o1 |
| PK04_098180 | | COCCOC(=O)N1C(=O)[C@]2([[C@@H][C@@H]3N([C@@H]2c4ccccc4OCCO)[C@H]([C@H](OC3=O)c5ccccc5)c6ccccc6)C(=O)N7CCc8cc(OC)c(OC)cc8C7)c9ccccc19 |
| SPBio_000230 | obtusaquinone | COC/1=CC(=O)C(=C\C1=C/C=C/c2ccccc2)O |
| PK04_097256 | | Oc1ccc(cc1)(C@@H]2N3[C@H]([C@H](C(=O)N4CCN(CC4)c5nccccn 5)[C@@]26C(=O)Nc7ccccc76)c(=O)O[C@H]([C@H]3c8ccccc8)c9ccccc9 |
| Maybridge4_000309 | | Cn1cc(c(n1)C(F)(F)F)S(=O)(=O)NCc2ccc3OCOc3c2 |
| BiomolKI2_000043 | | Brc1ccc(/C=C/CNCCNS(=O)(=O)c2cccc3cnccc23)cc1 |
| ChemDiv3_000369 | | CCOC(=O)n1c(=S)oc2ccccc12 |
| PK04_097173 | | COC(=O)C(CC#Cc1ccc2NC(=O)[C@]3([C@@H]([C@@H]4N([C@@H]3c5ccc(OCCO)cc5)[C@H]([C@@H](OC4=O)c6ccccc6)c7ccccc7)C(=O)NC[C@H](O)c8ccccc8)c2c1)C(=O)OC |
| HSCl1_000304 | Denbufylline | CCCCn1c(=O)n(CCCC)c2ncn(CC(=O)C)c2c1=O |
| ACon1_001926 | NP-005647 | COc1c(C2OCC(O)C(C2O)c(O)cc3oc(cc(=O)c13)c4ccc(OC5OC(C)C(O)C(O)C5O)cc4 |
| ChemDiv3_011138 | | COc1ccc(CNC(=O)Cc2cccs2)cc1OC |
| ChemDiv3_005090 | | O=C1c2ncn(c2C(=O)c3ccccc13)c4ccccc4 |
| TimTec1_006662 | | O=C(N1CCCC1)c2ccc3OCOc3c2 |
| ChemDiv3_011895 | | Cc1cc(C)c2c(CC(=O)Nc3c(oc4ccccc34)C(=O)c5ccccc5)coc2c1 |
| Maybridge4_003457 | | CNC(=S)C1(CC2CC3CC(C2)C1)C3 |
| PK04_097175 | | OCCOc1ccccc1[COH]2N3[C@@H]([C@@H](C(=O)N4CCN(CC4)c5nccn5)[C@]26C(=O)Nc7ccc(C#CC8(O)CCCCCC8)cc76)C(=O)O[COOH]([C@@H]3c9ccccc9)c%10ccccc%10 |

Example 2

Evaluation of Inhibitor Selectivity

Detail Protocol for MVK Assay
Quantities Per Single Well:

| Mix I (all in microL) | |
|---|---|
| MVK (any concentration) | 1 |
| 2× buffer | 20 |
| dH$_2$O | 19 |
| total: | 40 |

| Mix II (all in microL) | |
|---|---|
| 2× buffer | 10 |
| mevalonolactone [100 mM] | 0.6 (1 mM final concentration) |
| ATP [20 mM] | 0.015 (5 microM final concentration) |
| dH2O | 9.385 |
| total: | 20 |
| Kinase Glo | 30 |

Protocol: Mix I was prepared as above. (1 microL was used for MVK). If dilutions are to be made, dilute in 1× buffer to 1 microL. Mix II was prepared as above. Mix II was prepared just before use, as mevalonate and ATP may deteriorate. Mix II was kept on ice until it was dispensed.

At least 4 replicates per condition were conducted. Mix I was pipetted first onto the plate followed by Mix II. The plate was then covered with foil and incubated at 37° C. for 15 minutes. Kinase Glo was then added, the plate covered with foil, and incubated at room temperature (RT) for 15 minutes. The readings were measure as per the GALK protocol. The data were plotted and the enzyme concentration with reading within linear range just above baseline was selected. The optimal concentration was chosen to run the inhibitor test.

Protocol to test for inhibition: If the compounds were frozen, at −80° C. they were thawed slowly. Compound was kept at 10 mM stock concentration. 2 microL was added to 498 microL of Mix I to give 40 microM concentration. This dilution was used to create serial dilutions by mixing with mix I solution that did not contain the candidate inhibitor as set forth below:

| Mix I (no inhibitor) | Mix I (with inhibitor) | Compound concentration (microM) |
|---|---|---|
| 280 | 0 | 0 |
| 279 | 1 | 0.14 |
| 275 | 5 | 0.71 |
| 270 | 10 | 1.43 |
| 200 | 80 | 11.43 |
| 0 | 280 | 40 |

The mixtures were incubated for 1 hour with MVK. Each dilution can be pipetted into 5 wells (40 microL each). 20 microL of Mix II was added to each well and cover with foil and incubated at 37° C. for 15 min. Kinase-Glo® (Promega Madison, Wis.) was added and the wells were covered with foil. The reactions were incubated at RT for 15 minutes. The data were plotted and the $IC_{50}$ was calculated.

Detailed Protocol for CDP-ME Kinase Assay
Quantities Per Single Well:

| Mix I (all in microL) | |
|---|---|
| CMP kinase (any concentration) | 1 |
| 2× buffer | 20 |
| dH$_2$O | 19 |
| total: | 40 microL |
| Mix II (all in microL) | |
| 2× buffer | 10 |
| CMP-ME [10 mM] stock | 0.3 (50 microM final concentration) |
| ATP [20 mM] stock | 0.015 (5 microM final concentration) |
| dH$_2$O | 9.685 |
| total: | 20 microL |
| Kinase Glo | 30 microL |

Protocol: Mix I was prepared using 1 microL for MVK. If dilutions are to be made, dilute in 1× buffer to 1 microL. Mix II was prepared just before use, as CMP-ME and ATP may deteriorate. Final CMP-ME concentration was chosen at 50 microM for the sake of economics and kept on ice until it was dispensed.

At least 4 replicates per condition were used in the experiment. Mix I was dispensed on the plate with a pipette. Mix II was then added and the plate covered with foil. The plates was incubated at 37° C. for 15 minutes and Kinase-Glo® (Promega, Madison, Wis.) was added, the plate covered with foil, and incubated at RT for 15 minutes. Measurements were taken as described for the GALK protocol, the data were plotted and the enzyme concentration with reading within linear range just above baseline was selected. Once the concentration of MVK at which to run the inhibitory assay was established, the optimal concentration to run the next (inhibitor) test.

Protocol to test for inhibition: Compound stored at −80° C. was slowly thawed. Stock was at 10 mM concentration. 2 microL of compound was added to 498 microL of Mix I—this gave a 40 microM concentration. This dilution was used to create serial dilutions by mixing with Mix I solution that did not contain the candidate inhibitor:

| Mix I (no inhibitor) | Mix I (with inhibitor at 40 mM) | Compound (microM) |
|---|---|---|
| 280 | 0 | 0 |
| 280 | 1 | 0.14 |
| 276 | 5 | 0.17 |
| 271 | 10 | 1.43 |
| 201 | 80 | 11.43 |
| 0 | 280 | 40 |

These were incubated for 1 hour with MVK. Each dilution was then be pipetted into wells (40 microL each). 20 microL of Mix II was added to each well and covered with foil. The plates were incubated at 37° C., for 15 minutes, then Kinase-Glo® (Promega, Madison, Wis.) was added, plates were covered with foil, and incubated at room temperature (RT) for 15 minutes. The data was plotted and the $IC_{50}$ was calculated.

Figure 8:
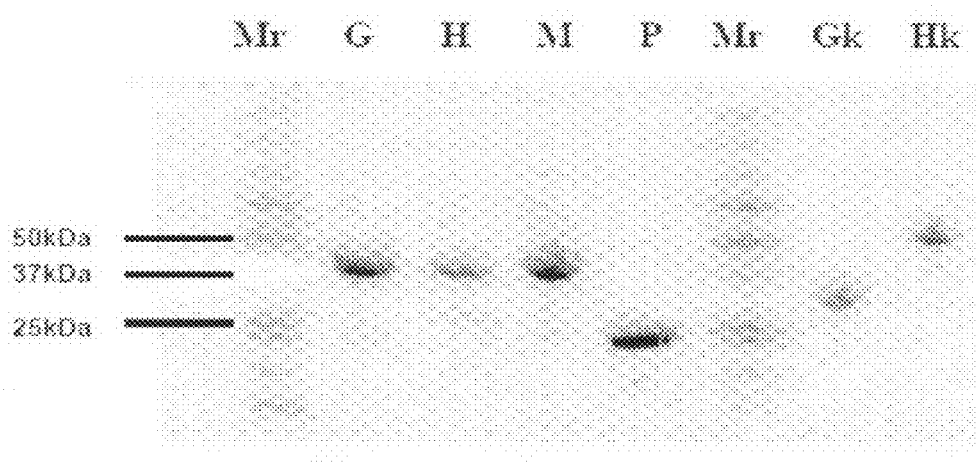
FIG. 8 is a photograph of a gel showing the GALK Selectivity Panel 1. Purified recombinant enzymes of the GHMP (Galactose, Homoserine, Mevalonate, Phosphomevalonate) kinases were loaded on SDS-PAGE along side with glucokinase (Gk) and hexokinase (Hk). Mr: Molecular weight markers.

Results:

To evaluate the selectivity of the selected compounds, these compounds were tested for their inhibitory properties against recombinant homoserine kinase, mevalonate kinase (MVK), and phosphomevalonate kinase (members of the GHMP kinases superfamily) which were purified by us, as well as glucokinase and hexokinase purchased from Sigma-Aldrich Inc. (cat. no.: G8887 and H6380, respectively) (FIG. 8). In these cases, galactose was replaced in the established luminescence-based GALK assay with the corresponding small molecules (i.e., mevalonic acid, homoserine or glucose) in the assays. It was found that slightly more than half of the compounds showed varying degrees of cross-inhibition towards the other members of GHMP kinases family, but none of them inhibited glucokinase and hexokinase.

As soon as it was realized that some compounds inhibit other members of the GHMP kinase superfamily, such as mevalonate kinase, experiments were conducted on the newer member of the family, 4-(Cytidine-5'-diphospho)-2-C-methyl-D-erythritol kinase (CDP-ME kinase). This enzyme is very unique and is present exclusively in eubacteria, chlamydia, and protozoa (Shi, W., et al., *J Biochem Mol Biol*, (2007) 40(6): p. 911-20; Wada, T., et al., *J Biol Chem*., (2003) 278 (32): p. 30022-7). Due to its absence in humans and higher animals and its role in isoprenoids biosynthesis in microbes, CDP-ME kinase was an ideal target for developing novel antimicrobials against pathogenic microbes such as *E. coli, Mycobacterium tuberculosis*, and *Plasmodium falciparum*.

The latter two pathogens killed more than two million people worldwide in 2006 (www.who.int/en/). For *Mycobacterium tuberculosis* (the causative agent for TB), the emergence of multiple drug-resistant (MDR) and extensive drug-resistant (XDR) tubercle bacillus strains only exacerbates the grave threat to the vulnerable populations, which include individuals who are either immuno-suppressed, immuno-compromised, or suffering from malnutrition and poor sanitation conditions. In contrast, malaria kills indiscriminately with regards to the health status of the patients and multiple drug-resistant *Plasmodium falciparum* strains are also on the rise.

Figure 9:
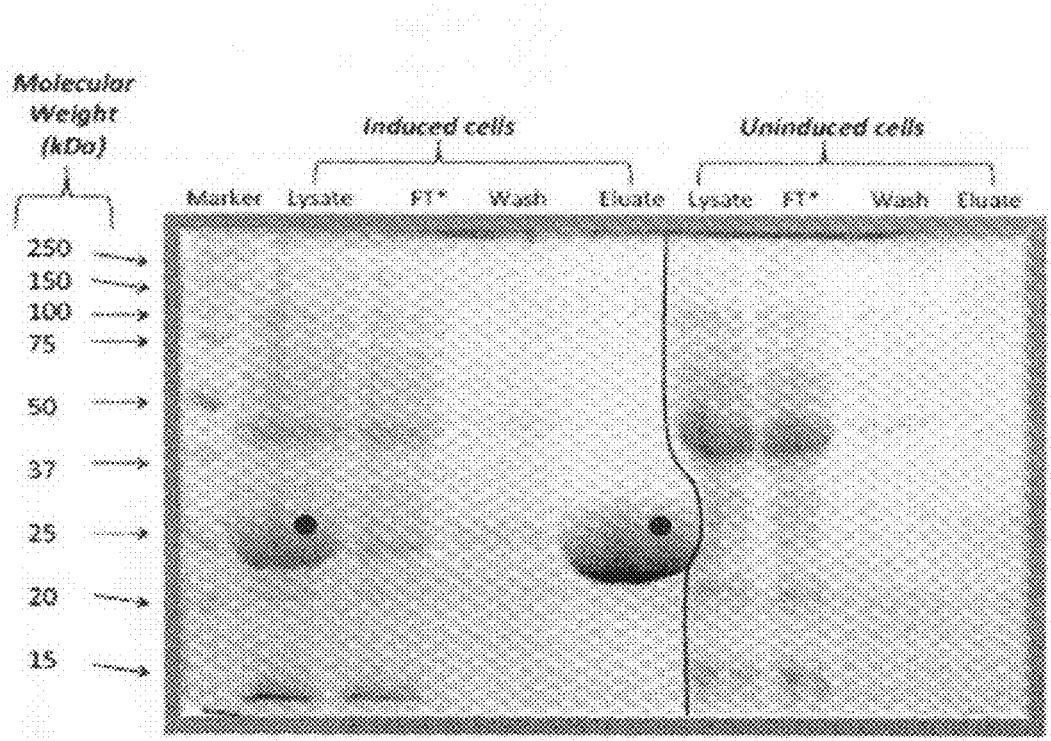
Figure 10B:
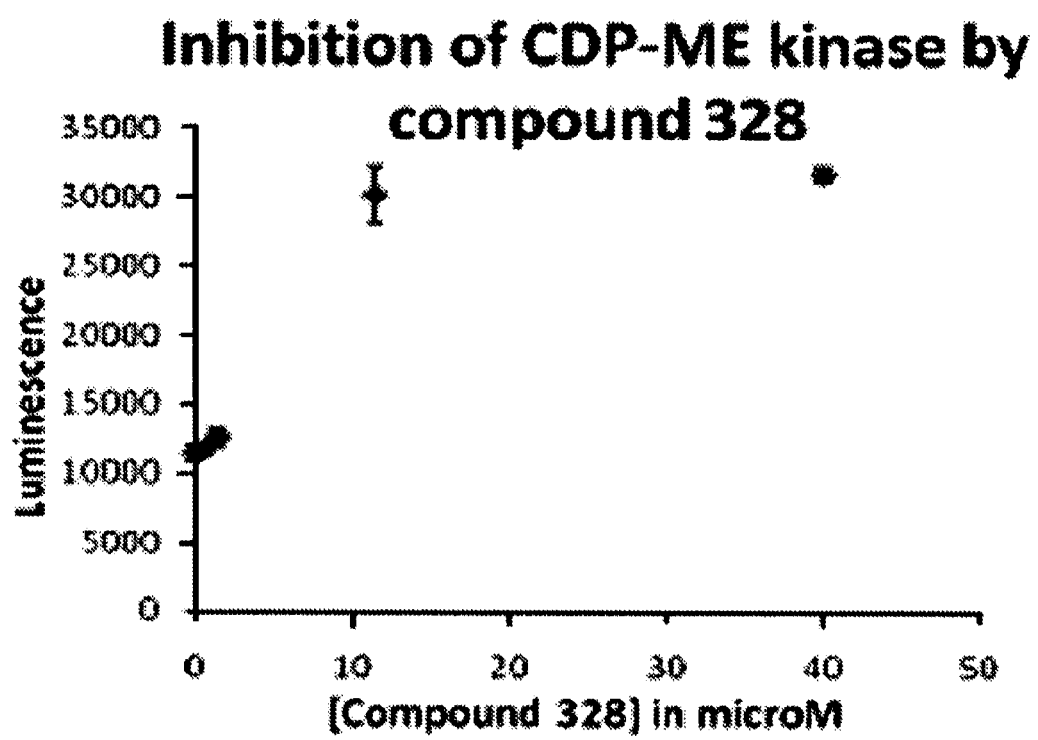
FIG. 10B is a graph showing increasing concentration of compound 328 inhibits E. coli CDP-ME kinase. Activity of purified CDP-ME kinase was measured in the presence of increasing amount of compound 328 (SPBio_001210).

Using CDP-ME as a substrate in a luminescence-based assay similar to the one developed for GALK as described above, a number of the GALK inhibitors were tested for their capabilities to inhibit purified recombinant *E. coli* CDP-ME kinase (FIGS. 9 and 10A, 10B). At least three compounds were found to inhibit *E. coli* CDP-ME kinase at a concentration comparable to, if not lower than; the level used to inhibit GALK.

FIG. 10A shows the results obtained in the validation of CDP-ME kinase assay. A two-step luminescence-based assay was used to test the activity of purified CDP-ME kinase by measuring the amount of ATP left in the reaction. Panel (a) showed that in the presence of active CDP-ME kinase, ATP was used up in the CDP-ME kinase reaction (first step), leaving little for the luciferase-luciferin reaction in step 2. FIG. 10B showed that increasing concentration of compound 328 inhibits *E. coli* CDP-ME kinase. Activity of purified CDP-ME kinase was measured in the presence of increasing amount of compound 328 (SPBio_001210).

What is claimed is:

1. A method of inhibiting galactokinase (GALK) in a cell, comprising:
administering to a cell, a composition comprising at least one agent selected from the group consisting of:

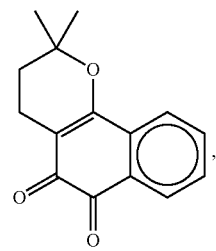

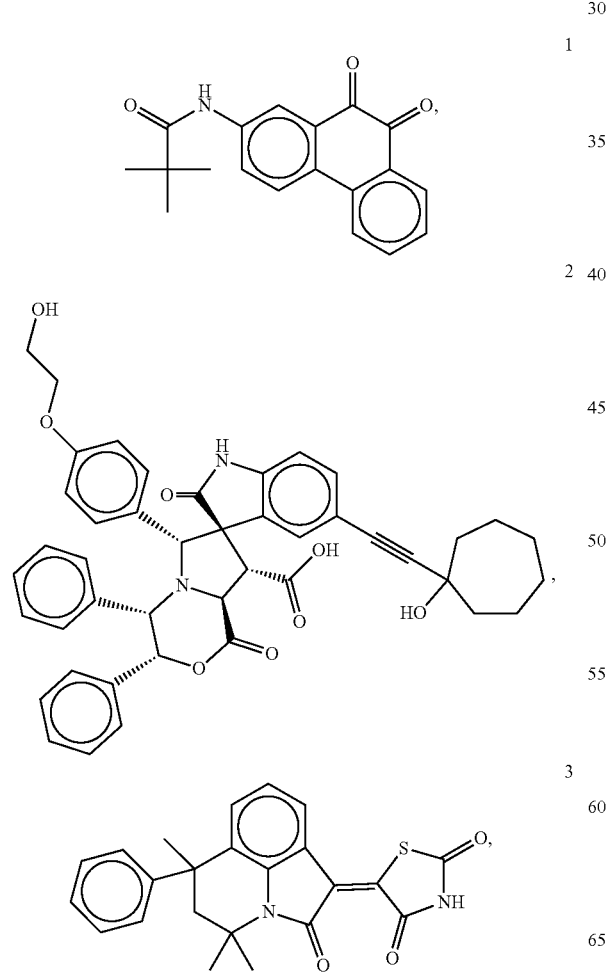

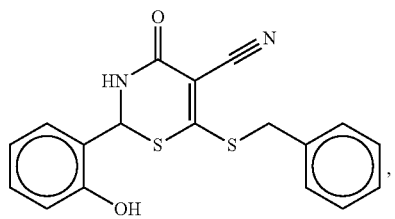

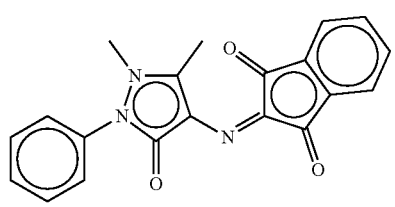

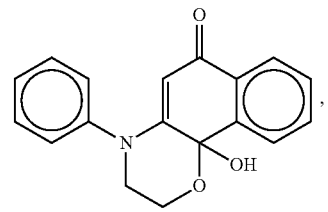

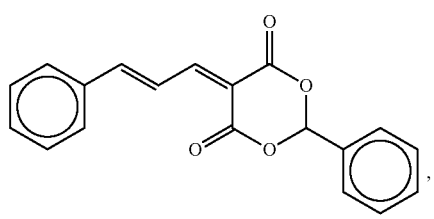

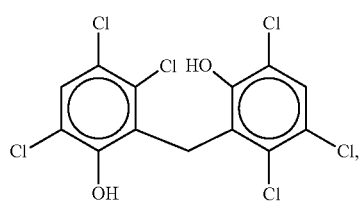

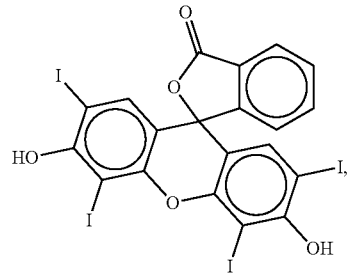

-continued
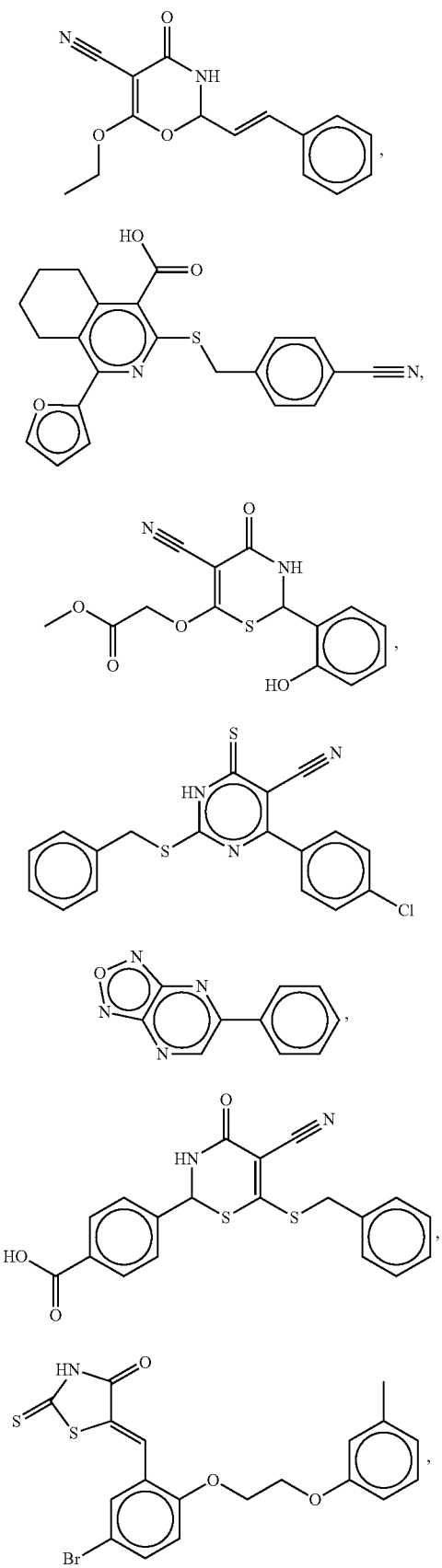
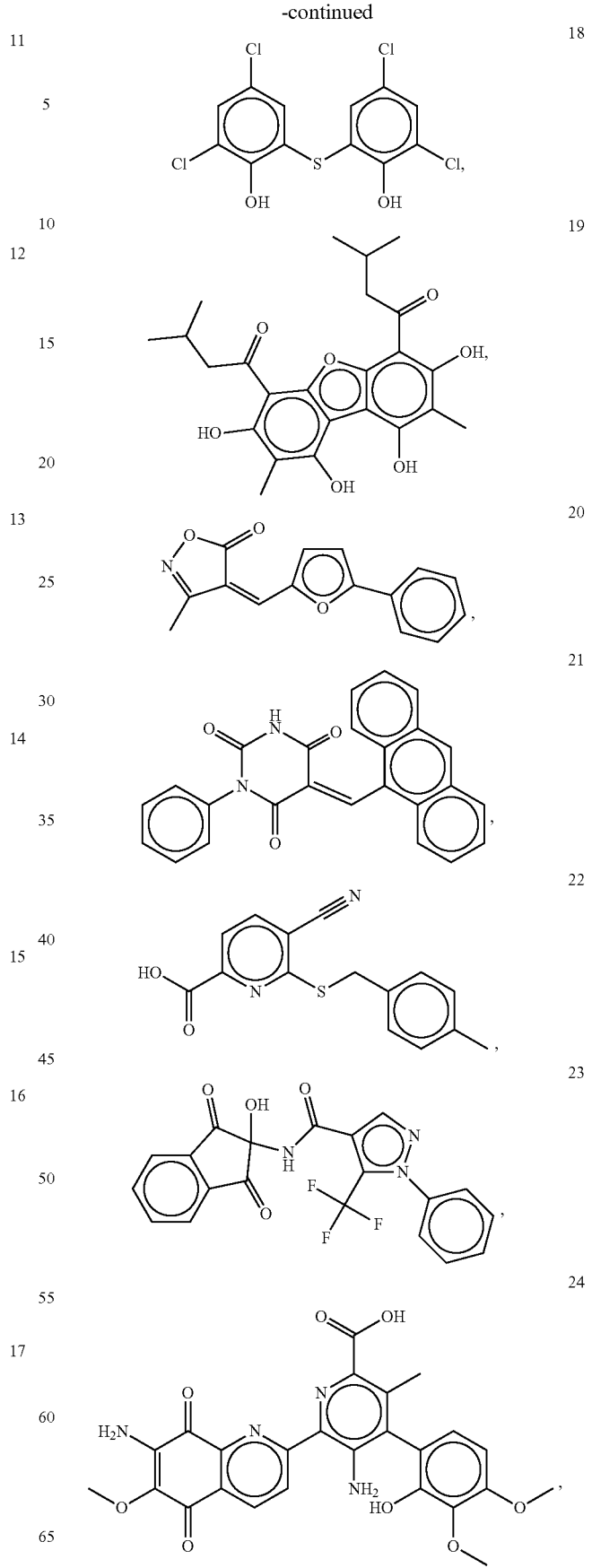

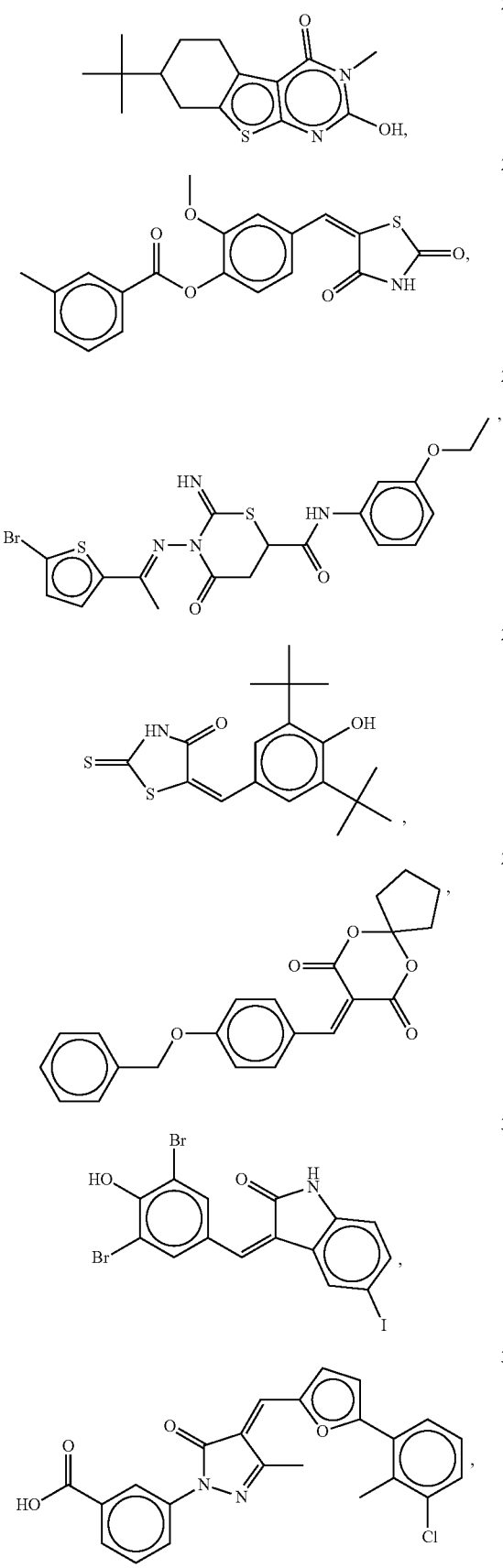
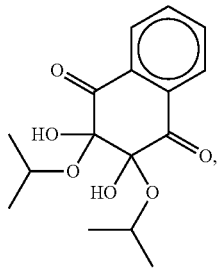
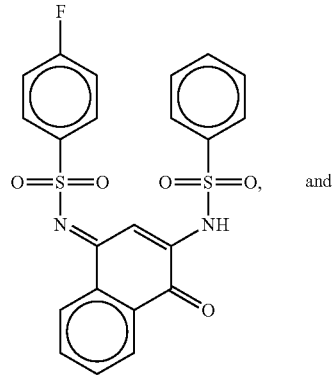
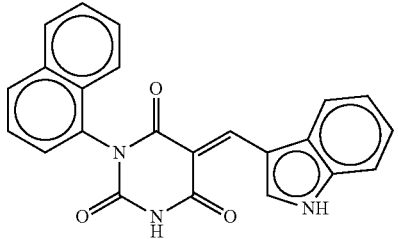
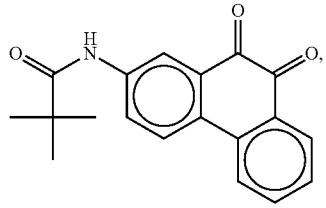
in a therapeutically effective amount for decreasing gal-1-p levels in the cell and inhibiting GALK in the cell.
2. The method of claim 1, wherein the at least one agent is selected from the group consisting of:
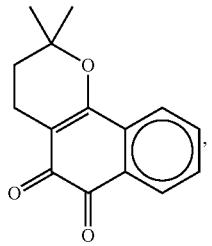

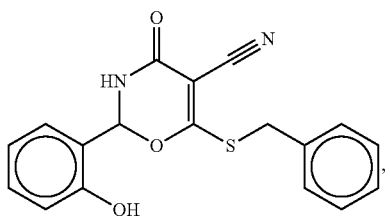
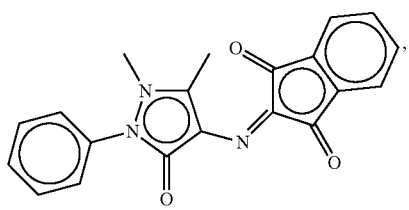
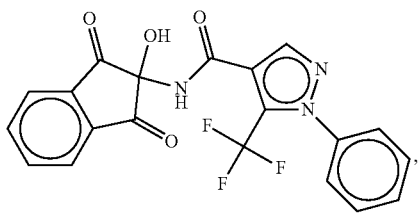
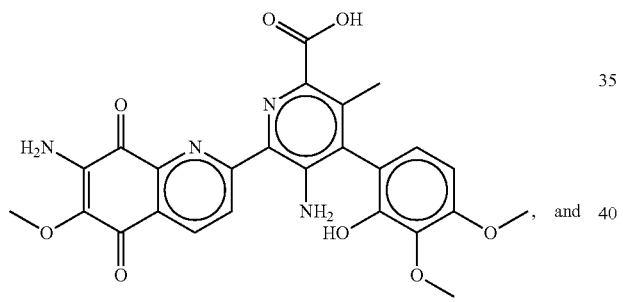
, and
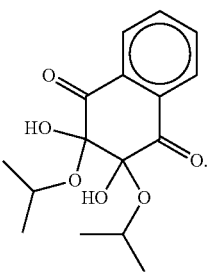
3. The method of claim 1, wherein the at least one agent is
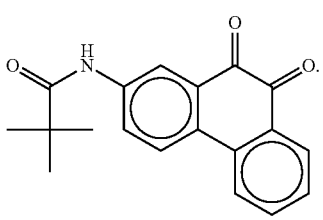
4. The method of claim 1, wherein the at least one agent is
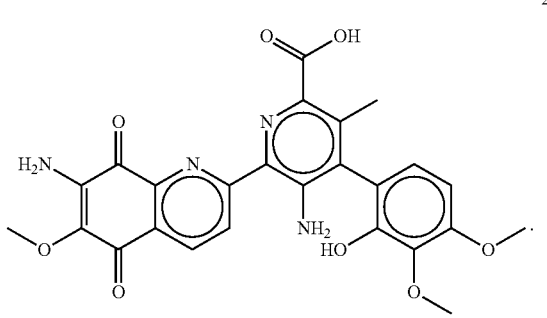
* * * * *

UNITED STATES PATENT AND TRADEMARK OFFICE
CERTIFICATE OF CORRECTION

| | | |
|---|---|---|
| PATENT NO. | : 8,357,701 B2 | |
| APPLICATION NO. | : 12/672347 | |
| DATED | : January 22, 2013 | |
| INVENTOR(S) | : Kent Lai et al. | |

It is certified that error appears in the above-identified patent and that said Letters Patent is hereby corrected as shown below:

On title page 1, column 1, under (75) Inventors, the spelling for Inventor "Klass Jan Wierenga" should read -- Klaas Jan Wierenga --

Signed and Sealed this
Fourth Day of June, 2013

Teresa Stanek Rea
*Acting Director of the United States Patent and Trademark Office*